United States Patent
Otsuka

(10) Patent No.: US 10,565,474 B2
(45) Date of Patent: Feb. 18, 2020

(54) DATA PROCESSING APPARATUS, DATA DISPLAY SYSTEM, SAMPLE DATA OBTAINING SYSTEM, METHOD FOR PROCESSING DATA, AND COMPUTER-READABLE STORAGE MEDIUM

(71) Applicant: CANON KABUSHIKI KAISHA, Tokyo (JP)

(72) Inventor: Yoichi Otsuka, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 327 days.

(21) Appl. No.: 14/568,038

(22) Filed: Dec. 11, 2014

(65) Prior Publication Data
US 2015/0168292 A1 Jun. 18, 2015

(30) Foreign Application Priority Data

Dec. 17, 2013 (JP) ................................ 2013-260678
Oct. 14, 2014 (JP) ................................ 2014-210283

(51) Int. Cl.
*G01N 33/48* (2006.01)
*G01N 33/50* (2006.01)
*G06K 9/62* (2006.01)

(52) U.S. Cl.
CPC .................................. *G06K 9/6242* (2013.01)

(58) Field of Classification Search
None
See application file for complete search history.

(56) References Cited

U.S. PATENT DOCUMENTS

2004/0248317 A1* 12/2004 Swamy .............. G01N 33/6842
436/173
2006/0058983 A1 3/2006 Araki

FOREIGN PATENT DOCUMENTS

| JP | 2006-084425 A | 3/2006 |
| JP | 2009-134466 A | 6/2009 |
| JP | 2012-528327 A | 11/2012 |
| JP | 2013-160576 A | 8/2013 |

OTHER PUBLICATIONS

Vrabie et al. Independenty component analysis of Raman spectra: Application on paraffin-embedded skin biopsies. Biomedical Signal Processing and Control, vol. 2, 2007, pp. 40-50.*
Lin et al. Multivariate analysis of neuronal interactions in the generalized partial least squares framework: simulations and empirical studies. NeuroImage, vol. 20, pp. 625-642. (Year: 2003).*
Y. Ozeki et al., High-speed molecular spectral imaging of tissue with stimulated Raman scattering, Nature Photonics 6, pp. 845-851 (2012).
Gabriel Martin, et al, "Region-Based Spatial Preprocessing for Endmember Extraction and Spectral Unmixing", IEEE Geoscience and Remote Sensing Letters, vol. 8, No. 4, Jul. 2011, pp. 745-749.
Supplementary Information, DOI: 10.1038/NPHOTON. 2012.263, Nature photonics, 2012 Macmillan Publishers Limited., pp. 1-10.
Yoichi Otsuka et al., "High-speed stimulated Rama spectral imaging for digital staining of mouse cancer tissue", Proc. of SPIE vol. 894, pp. 89470C-1 through 89470C-8, 2014.
Martin Hedegaard et al., "Spectral unmixing and clustering algorithms for assessment of single cells by Raman microscopic imaging", Theor Chem Acc (2011) 130:1249-1260.

* cited by examiner

*Primary Examiner* — Russell S Negin
(74) *Attorney, Agent, or Firm* — Canon U.S.A., Inc. IP Division

(57) ABSTRACT

A data processing apparatus that processes data including a plurality of spectra includes a group setting unit, an extracted data generation unit, and a base vector obtaining unit. The group setting unit classifies the plurality of spectra into a plurality of groups. The extracted data generation unit selects at least one spectrum from each of the groups set by the group setting unit and generates extracted data including the selected spectra. The base vector obtaining unit obtains, from the extracted data generated by the extracted data generation unit, base vectors for attributing the spectra to corresponding components.

17 Claims, 15 Drawing Sheets

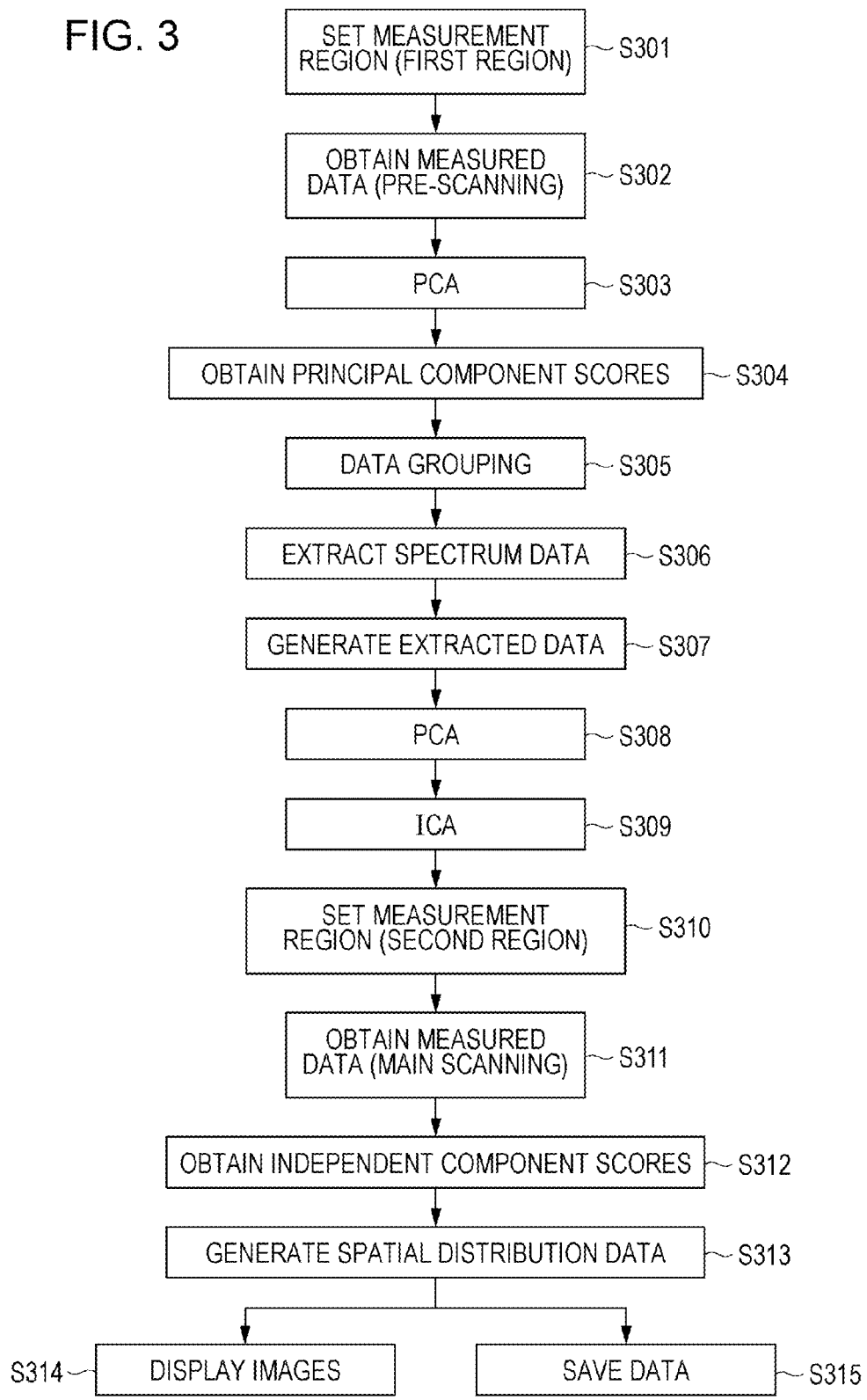

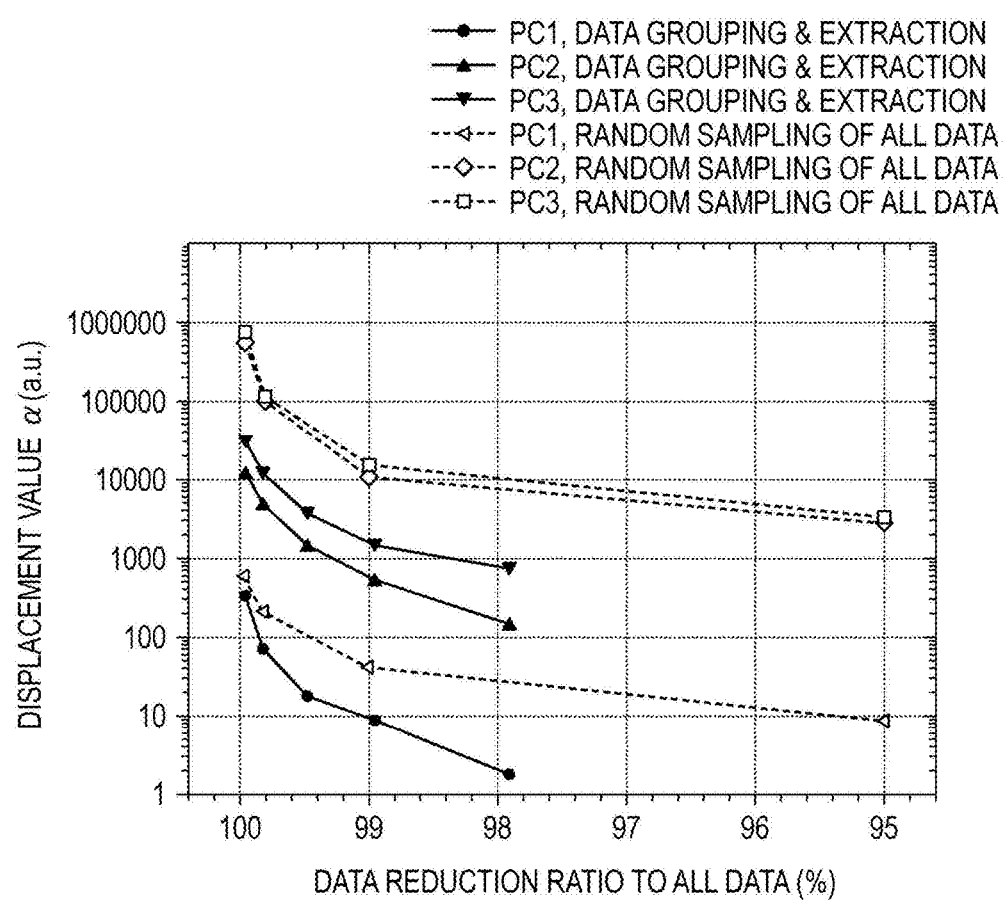

FIG. 11

| RAMAN SHIFT NUMBER | RAMAN SHIFT WAVENUMBER (cm⁻¹) | DATA SET NUMBER 1 | 2 | 3 | 4 |
|---|---|---|---|---|---|
| 0 | 2800 | ● | ● | ● | ● |
| 1 | 2803.3 |  |  |  | ● |
| 2 | 2806.7 |  |  |  | ● |
| 3 | 2810 |  |  | ● | ● |
| 4 | 2813.3 |  |  |  | ● |
| 5 | 2816.7 |  | ● |  | ● |
| 6 | 2820 |  |  | ● | ● |
| 7 | 2823.3 |  |  |  | ● |
| 8 | 2826.7 |  |  |  | ● |
| 9 | 2830 |  |  | ● | ● |
| 10 | 2833.3 | ● | ● |  | ● |
| 11 | 2836.7 |  |  |  | ● |
| 12 | 2840 |  |  | ● | ● |
| 13 | 2843.3 |  |  |  | ● |
| 14 | 2846.7 |  |  |  | ● |
| 15 | 2850 |  | ● | ● | ● |
| 16 | 2853.3 |  |  |  | ● |
| 17 | 2856.7 |  |  |  | ● |
| 18 | 2860 |  |  | ● | ● |
| 19 | 2863.3 |  |  |  | ● |
| 20 | 2866.7 | ● | ● |  | ● |
| 21 | 2870 |  |  | ● | ● |
| 22 | 2873.3 |  |  |  | ● |
| 23 | 2876.7 |  |  |  | ● |
| 24 | 2880 |  |  | ● | ● |
| 25 | 2883.3 |  | ● |  | ● |
| 26 | 2886.7 |  |  |  | ● |
| 27 | 2890 |  |  | ● | ● |
| 28 | 2893.3 |  |  |  | ● |
| 29 | 2896.7 |  |  |  | ● |
| 30 | 2900 | ● | ● | ● | ● |
| 31 | 2903.3 |  |  |  | ● |
| 32 | 2906.7 |  |  |  | ● |
| 33 | 2910 |  |  | ● | ● |
| 34 | 2913.3 |  |  |  | ● |
| 35 | 2916.7 |  | ● |  | ● |
| 36 | 2920 |  |  | ● | ● |
| 37 | 2923.3 |  |  |  | ● |
| 38 | 2926.7 |  |  |  | ● |
| 39 | 2930 |  |  | ● | ● |
| 40 | 2933.3 | ● | ● |  | ● |
| 41 | 2936.7 |  |  |  | ● |
| 42 | 2940 |  |  | ● | ● |
| 43 | 2943.3 |  |  |  | ● |
| 44 | 2946.7 |  |  |  | ● |
| 45 | 2950 |  |  | ● | ● |
| 46 | 2953.3 |  |  |  | ● |
| 47 | 2956.7 |  |  |  | ● |
| 48 | 2960 |  |  | ● | ● |
| 49 | 2963.3 |  |  |  | ● |
| 50 | 2966.7 | ● | ● |  | ● |
| 51 | 2970 |  |  | ● | ● |
| 52 | 2973.3 |  |  |  | ● |
| 53 | 2976.7 |  |  |  | ● |
| 54 | 2980 |  |  | ● | ● |
| 55 | 2983.3 |  | ● |  | ● |
| 56 | 2986.7 |  |  |  | ● |
| 57 | 2990 |  |  | ● | ● |
| 58 | 2993.3 |  |  |  | ● |
| 59 | 2996.7 |  |  |  | ● |
| 60 | 3000 | ● | ● | ● | ● |
| 61 | 3003.3 |  |  |  | ● |
| 62 | 3006.7 |  |  |  | ● |
| 63 | 3010 |  |  | ● | ● |
| 64 | 3013.3 |  |  |  | ● |
| 65 | 3016.7 |  | ● |  | ● |
| 66 | 3020 |  |  | ● | ● |
| 67 | 3023.3 |  |  |  | ● |
| 68 | 3026.7 |  |  |  | ● |
| 69 | 3030 |  |  | ● | ● |
| 70 | 3033.3 | ● | ● |  | ● |
| 71 | 3036.7 |  |  |  | ● |
| 72 | 3040 |  |  | ● | ● |
| 73 | 3043.3 |  |  |  | ● |
| 74 | 3046.7 |  |  |  | ● |
| 75 | 3050 |  | ● | ● | ● |
| 76 | 3053.3 |  |  |  | ● |
| 77 | 3056.7 |  |  |  | ● |
| 78 | 3060 |  |  | ● | ● |
| 79 | 3063.3 |  |  |  | ● |
| 80 | 3066.7 | ● | ● |  | ● |
| 81 | 3070 |  |  | ● | ● |
| 82 | 3073.3 |  |  |  | ● |
| 83 | 3076.7 |  |  |  | ● |
| 84 | 3080 |  |  | ● | ● |
| 85 | 3083.3 |  | ● |  | ● |
| 86 | 3086.7 |  |  |  | ● |
| 87 | 3090 |  |  | ● | ● |
| 88 | 3093.3 |  |  |  | ● |
| 89 | 3096.7 |  |  |  | ● |
| 90 | 3100 |  |  |  | ● |

DATA PROCESSING APPARATUS, DATA DISPLAY SYSTEM, SAMPLE DATA OBTAINING SYSTEM, METHOD FOR PROCESSING DATA, AND COMPUTER-READABLE STORAGE MEDIUM

BACKGROUND

Technical Field

The present disclosure relates to an apparatus that processes data including a plurality of spectra and a method for processing the data.

Description of the Related Art

Biological tissues include various substances. In order to detect differences in the composition and the chemical state of the substances, various spectra of a biological sample are measured, and the measured spectra are analyzed. By setting a plurality of measurement points in the biological sample and analyzing spectra measured at the measurement points, spatial distribution information such as the shapes and the composition of the biological tissues can be obtained without staining the biological sample.

Currently, multivariate analyses typified by a principal component analysis (PCA) and an independent component analysis (ICA) are adopted as methods for analyzing spectra.

Since a biological sample includes a plurality of components and tissues, spectra derived from these components are superimposed upon one another, and accordingly spectra obtained as a result of measurement of the biological sample are complex. By using the multivariate analyses, the spectra derived from the components of the sample can be separated from one another in these complex spectra, thereby making it possible to analyze the components and the composition.

In Y. Ozeki et al. "High-speed molecular spectral imaging of tissue with stimulated Raman scattering", Nature Photonics 6, pp. 845-851 (2012), a method is described in which Raman spectra are measured at a plurality of measurement points in a biological sample and a PCA and an ICA are performed on data including the obtained plurality of spectra to obtain the spatial distribution of independent component scores. By using this method, spatial distribution information regarding components of the biological sample can be obtained. By using a different color for a spatial distribution image of each component and superimposing the spatial distribution images, the distribution of the components in the biological sample can be displayed in false colors.

In general, when a plurality of spectra of components of a sample are separated from one another in data including the plurality of spectra using an ICA, first, a separation matrix (base vectors) is obtained. Thereafter, the obtained separation matrix is applied to the spectra included in the data to obtain independent component scores.

The separation matrix is obtained by performing convergence calculation on a source matrix, which is obtained by applying the separation matrix to the data, in such a way as to maximize the statistical independence of each source vector in the source matrix. Therefore, as the amount of data subjected to the ICA, that is, the number of dimensions of spectra and the number of measurement points, increases, the amount of calculation and calculation time exponentially increase.

SUMMARY

Therefore, if observation is conducted in a broader region, that is, for example, if the entirety of a sample is observed or if observation is sequentially conducted in a plurality of fields of view, it takes time to process data, which is problematic.

Therefore, a data processing apparatus that processes data including a plurality of spectra at high speed is provided.

A data processing apparatus for attributing a plurality of spectra included in data to a plurality of components using a plurality of first base vectors according to an aspect of the present invention includes a group setting unit configured to classify the plurality of spectra into a plurality of groups using a plurality of second base vectors, an extracted data generation unit configured to generate extracted data by extracting each one or more spectrum from each of the plurality of groups, and a base vector obtaining unit configured to obtain the plurality of first base vectors from the extracted data.

BRIEF DESCRIPTION OF THE DRAWINGS

According to the data processing apparatus according to the aspect of the present invention, data including a plurality of spectra can be processed at high speed.

Further features of the present invention will become apparent from the following description of exemplary embodiments with reference to the attached drawings.

FIG. 3 is a flowchart illustrating an operation performed by a sample data obtaining system including a data processing apparatus according to a second embodiment.

FIG. 7 is a diagram illustrating a correlation between variation in the eigenvectors and a data reduction ratio in the first example.

FIG. 11 is a diagram illustrating data sets whose wavenumbers have been reduced in a second example.

DESCRIPTION OF THE EMBODIMENTS

First Embodiment

A data processing apparatus 1 according to a first embodiment will be described with reference to FIGS. 1 and 2.

Figure 1:
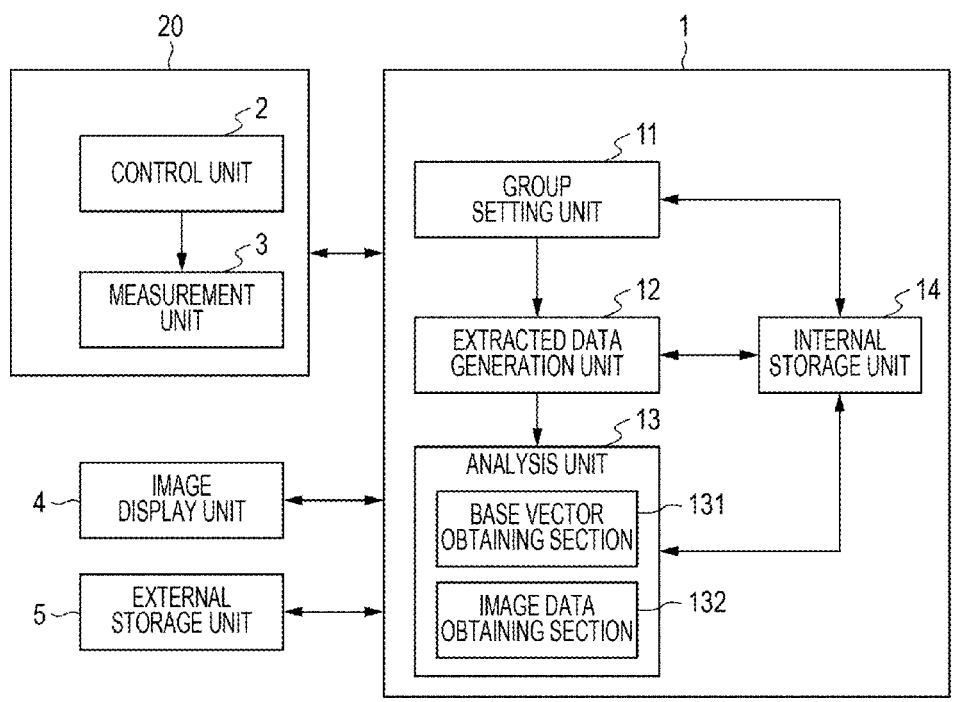
FIG. 1 is a block diagram illustrating an example of the configuration of a sample data obtaining system including a data processing apparatus according to a first embodiment.
Figure 2:
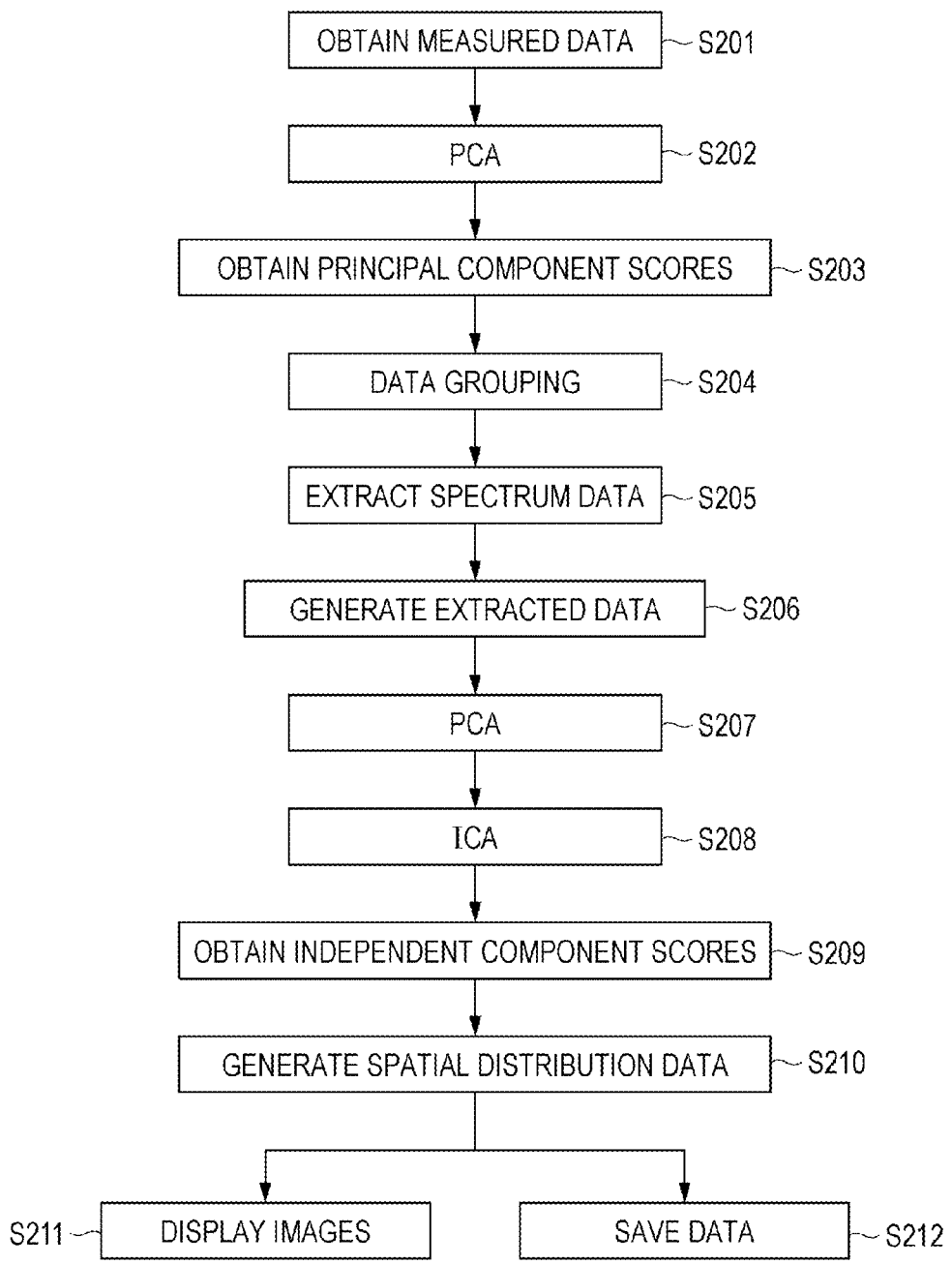
FIG. 2 is a flowchart illustrating an operation performed by the sample data obtaining system including the data processing apparatus according to the first embodiment.

FIG. 1 is a block diagram illustrating the configuration of a sample data obtaining system including the data processing apparatus 1 according to this embodiment.

The sample data obtaining system according to this embodiment includes the data processing apparatus 1, a control unit 2, a measurement unit 3, an image display unit 4, and an external storage unit 5. Here, some or all of the data processing apparatus 1, the control unit 2, the measurement unit 3, the image display unit 4, and the external storage unit 5 may be connected to one another through a network. The network includes a local area network (LAN) and the Internet.

The measurement unit 3, which is controlled by the control unit 2, measures a plurality of spectra of a sample, which is not illustrated, and generates data including the plurality of spectra. "Spectra" herein refer to, for example, data obtained by storing the intensity of responses generated for measurement parameters (various types of stimulation) when a sample is stimulated. Examples of the stimulation include an electromagnetic wave, a sound, an electromagnetic field, a temperature, and a value of humidity. Spectra include absorption spectra, reflectance spectra or transmission spectra in an ultraviolet range, a visible range, or an infrared range, Raman spectra, nuclear magnetic resonance (NMR) spectra, mass spectra, liquid chromatograms, gas chromatograms, and sound frequency spectra. The Raman spectra include spontaneous Raman scattering spectra and nonlinear Raman scattering spectra. Nonlinear Raman scattering spectroscopy may be stimulated Raman scattering (SRS), coherent anti-stokes Raman scattering (CARS), or coherent stokes Raman scattering (CSRS). In this embodiment, the spectra may include any of spectroscopy spectra in the ultraviolet range, the visible range, or the infrared range, Raman spectra, and mass spectra.

The image display unit 4 obtains image data such as spatial intensity distribution data including independent component scores and principal component score, which will be described later, and displays the image data as images.

The external storage unit 5 stores the image data such as the spatial intensity distribution data including the independent component scores and the principal component scores, which will be described later. The stored image data can be read and displayed on the image display unit 4 as images as necessary. In addition, data including a plurality of spectra measured and generated by another apparatus may be stored in the external storage unit 5 in advance. The data may then be read and transmitted to the data processing apparatus 1 as necessary, and the data processing apparatus 1 may process the data.

The data processing apparatus 1 includes a group setting unit 11, an extracted data generation unit 12, an analysis unit 13, and an internal storage unit 14.

The group setting unit 11 sets two or more groups on the basis of similarity in information included in a plurality of spectra included in data obtained from the measurement unit 3 or the external storage unit 5 using second base vectors. That is, the group setting unit 11 classifies the plurality of spectra included in the data obtained from the measurement unit 3 or the external storage unit 5 into a plurality of groups. The setting of groups performed by the group setting unit 11 will be referred to as "data grouping" hereinafter.

The extracted data generation unit 12 selects at least one of the spectra included in each group set by the group setting unit 11 and generates extracted data including the selected spectra. As a result, the extracted data generation unit 12 can generate the extracted data including a smaller number of pieces of data than the original data.

The analysis unit 13 analyzes the data obtained from the measurement unit 3 or the external storage unit 5 and attributes the spectra to corresponding components in order to generate image data indicating the spatial distribution of the components. The analysis unit 13 includes a base vector obtaining section 131 and an image data obtaining section 132.

The base vector obtaining section 131 obtains base vectors for attributing the spectra obtained from the measurement unit 3 or the external storage unit 5 to the corresponding components. The base vector obtaining section 131 obtains the first base vectors of the extracted data by performing a multivariate analysis on the extracted data.

Here, the "multivariate analysis" is a statistical technique for analyzing a correlation between a plurality of variables on the basis of data regarding the plurality of variables. That is, in this embodiment, for example, the spectra can be classified and attributed to the corresponding components by analyzing the correlation between spectral components such as wavenumbers. A "base vector" herein is a criterion for determining a component to which each spectrum is attributed. By applying the base vectors to the spectra, dimensional compression can be realized, and scores for the base vectors corresponding to the components can be obtained. Each of the "components" herein may be a single substance or may be a mixture of a plurality of substances. That is, each of the components may be a certain type of molecule included in a sample whose spectra are measured or may be a tissue or a component including a plurality of molecules included in a sample whose spectra are measured.

The type of multivariate analysis used in this embodiment is not particularly limited, and various methods such as a principal component analysis, an independent component analysis, a factor analysis, a discriminant analysis, a cluster analysis, and a self-organizing map may be used.

The principal component analysis is a method for analyzing data by obtaining multiple axes (eigenvectors) that maximize variances of the multidimensional data. By using the eigenvectors, components included in the multidimensional data can be classified. That is, by performing the principal component analysis, the eigenvectors are obtained and the multidimensional data can be divided into main components (principal components).

The independent component analysis is a method for analyzing data by obtaining a matrix (separation matrix) that, when applied to multidimensional data, maximizes non-Gaussianity. By using the separation matrix, components included in the multidimensional data can be classified into components at a time when it is assumed that the multidimensional data is composed of statistically independent components (independent components).

Here, the principal component analysis and the independent component analysis both classify components included in the data, but these analyses are different in the following ways.

In the principal component analysis, eigenvectors are sequentially obtained on the basis of variances in a multidimensional space. Therefore, in data obtained after components included in the data are classified, spectral information held by original data is undesirably lost. For this reason, it is difficult to associate the eigenvectors, which are base vectors obtained as a result of the principal component analysis, with the original spectral information. Therefore, it is also difficult to identify components indicated by two-dimensional distribution images of score values calculated from the base vectors by associating the components with the spectral information. In order to identify the components by performing a component analysis using the principal component analysis, base vectors obtained by performing a principal component analysis on data whose components are known need to be obtained in advance.

In the independent component analysis, as described later, multiple independent component spectra can be separated from the data in which multiple spectra are mixed without prior information. Each independent component spectrum can be attributed to the original spectrum. Therefore, the obtained base vectors can be compared with the actual spectral information without analyzing in advance data whose components are known. That is, by using the independent component analysis, it becomes easier to analyze the components of an unknown sample than when the principal component analysis is used, which is advantageous.

On the other hand, because convergence calculation of a matrix corresponding to multidimensional data needs to be performed in the independent component analysis, the amount of calculation for a unit amount of data is larger than that of the principal component analysis, which means that a calculation process takes time. Therefore, a method is known in which multidimensional data is not directly analyzed using the independent component analysis but the dimensions of the multidimensional data are compressed by performing the principal component analysis and then the independent component analysis is performed in order to suppress calculation cost.

The image data obtaining section 132 obtains image data indicating the spatial distribution of the components by attributing the spectra to the corresponding components using the first base vectors obtained by the base vector obtaining section 131. As a result, multidimensional data including a plurality of spectra that cannot be displayed as images can be compressed into two-dimensional or three-dimensional data, and image data that can be displayed on the image display unit 4 as images can be obtained.

The image data obtaining section 132 obtains second score values using the first base vectors obtained by the base vector obtaining section 131 and the spectra included in the data obtained from the measurement unit 3 or the external storage unit 5. The type of second multivariate analysis is not particularly limited, but the PCA or the ICA may be used. If the second multivariate analysis is the PCA, eigenvectors are obtained as the first base vectors, and principal component scores are obtained as the second score values. On the other hand, if the second multivariate analysis is the ICA, separation vectors are obtained as the first base vectors, and independent component scores are obtained as the second score values. The image data obtaining section 132 can generate image data indicating the spatial distribution of components corresponding to the base vectors by generating spatial distribution data regarding the second score values obtained in this manner.

The internal storage unit 14 stores various pieces of data generated by the group setting unit 11, the extracted data generation unit 12, and the analysis unit 13.

Next, an operation performed by the sample data obtaining system including the data processing apparatus 1 according to this embodiment will be described with reference to FIG. 2.

The data processing apparatus 1 obtains data including a plurality of spectra from the measurement unit 3 or the external storage unit 5 (S201). The obtained data is stored in the internal storage unit 14 as necessary. Here, if the number of dimensions of the spectra is denoted by n and the number of measurement points is denoted by m, the obtained data can be expressed as an n×m matrix. The number of dimensions is determined by the number of data points included in the spectrum. For instance, the number of dimensions of Raman spectrum and mass spectrum can be determined by the number of data points which are obtained for different Raman shift and different mass to charge ratio, respectively.

The number of dimensions n is not particularly limited. That is, the number of dimensions n may be, for example, a maximum value of the number of dimensions of the spectra that can be measured by the measurement unit 3 or may be the number of dimensions arbitrarily selected within the maximum number of dimensions.

The group setting unit 11 performs the PCA on the obtained data as a first multivariate analysis (S202). When the group setting unit 11 performs the PCA on a data set, first, an n×n variance-covariance matrix is obtained from the n×m matrix of the data. For example, the n×n matrix may be obtained by multiplying the obtained data and a transposed matrix of the obtained data. In addition, the obtained n×n matrix may be normalized using the number of measurement points m. By solving this eigenvalue problem of the n×n matrix, eigenvectors and eigenvalues of the data are obtained.

The speed or the efficiency of the calculation process in the PCA can be increased by preprocessing the data before the PCA is performed. For example, an average of the values of spectral intensity is obtained for each spectrum, and the obtained average is subtracted from the spectral intensity of each spectrum. Alternatively, a normalization process for setting a maximum value of spectral intensity to a certain value (for example, 100) may be performed for each spectrum.

As a result of the calculation, n eigenvectors are obtained from the n×n matrix, but any number of eigenvectors may be selected from the n eigenvectors. As a method for selecting eigenvectors, a method based on eigenvalues corresponding to the eigenvectors may be used. For example, contribution percentages, each of which indicates the percentage of an eigenvalue relative to the sum of the eigenvalues corresponding to the eigenvectors, are obtained, and only eigenvectors corresponding to eigenvalues whose contribution percentages are equal to or larger than an arbitrary value are selected.

If k eigenvectors are selected from the n eigenvectors, for example, the eigenvectors may be selected by performing matrix calculation using a k×n matrix L, where L=(I0). Here, I denotes a unit matrix, and 0 denotes a null matrix.

Next, the group setting unit 11 obtains principal component scores, which are first score values corresponding to the eigenvectors of the spectra, by calculating inner products between the obtained eigenvectors (n dimensions), which are used as the second base vectors, and the corresponding spectra (n dimensions) (S203). Two different groups are generated from a single eigenvector. One group contains scores values that are equal to or above 0 and the other group contains scores values that are less than 0. The score values in the latter group may be changed by the absolute values of their own.

Next, the group setting unit 11 performs data grouping on the data on the basis of the obtained principal component scores (S204). In the data grouping, whether each principal component score satisfies an arbitrary value condition is determined, and if so, the coordinates of the measurement point of the spectrum corresponding to each principal component score is extracted and stored as a group. Alternatively, the spectrum itself may be extracted, and then a group may be generated and stored.

The value condition may be satisfied if each principal component score is equal to or larger than an arbitrary value or if each principal component score is smaller than or equal to an arbitrary value. Alternatively, an arbitrary range of values may be used as the value condition. For example, if k eigenvectors are selected and the value condition is satisfied if each principal component score is equal to or larger than 0, a total of 2k groups are generated because two groups are generated for each eigenvector. In this embodiment, an arbitrary number of groups are selected from these 2k groups.

In an example of the selection of groups, the image display unit 4 displays the spatial distribution of each group, and a group capable of representing a characteristic image is selected. Measurement points included in the generated groups may be compared with one another, and a set obtained by performing a set operation using the groups may be set as a new group and selected.

In this embodiment, the group setting unit 11 performs the PCA on the obtained data as the first multivariate analysis and then performs the data grouping on the basis of results of the PCA (S202 and S203). The first multivariate analysis, however, is not limited to the PCA, and another type of multivariate analysis may be performed as the first multivariate analysis, and the data grouping may be performed on the basis of results of the multivariate analysis. More specifically, the first multivariate analysis may be the ICA, the factor analysis, the discriminant analysis, the cluster analysis, or the like.

The first multivariate analysis may be a multivariate analysis whose amount of calculation for a unit amount of data is smaller than that of the second multivariate analysis. As described later, in this embodiment, the size of data subjected to the second multivariate analysis is reduced while certainly collecting minor components by extracting spectra for each group set on the basis of results of the first multivariate analysis. That is, by performing, before the second multivariate analysis, rough data grouping through the first multivariate analysis, which is a simpler analysis method than the second multivariate analysis, the time taken to complete the second multivariate analysis can be reduced.

Alternatively, the data grouping may be performed without the group setting unit 11 performing the first multivariate analysis. That is, results of the first multivariate analysis obtained in past data processing may be obtained from the internal storage unit 14 or the external storage unit 5, and the data grouping may be performed on the basis of the results. For example, eigenvectors obtained in the past data processing may be accumulated in the internal storage unit 14 or the external storage unit 5 as a database, and the first score values may be obtained using eigenvectors of similar data obtained from the database.

The extracted data generation unit 12 extracts measurement points or spectra included in each group at an arbitrary ratio (S205). The extraction of measurement points, that is, the extraction of spectra, may be realized by randomly extracting measurement points included in each group. Since the size of the extracted data generated as a result of the extraction is smaller than that of the original data, the amount of calculation performed in subsequent steps can be reduced, thereby realizing high-speed data processing.

The spectra are extracted such that the number of spectra included in each group becomes at least one. The spectra may be extracted such that the number of spectra included in each group becomes the same. In doing so, an effect of an uneven ratio of the number of spectra included in each group to the total number of spectra included in all the groups upon results of the calculation can be suppressed.

If the spectra are randomly extracted without performing the data grouping, groups including few spectra relative to the total number of spectra, that is, minor components, are likely to be neglected as the number of spectra extracted becomes smaller. By extracting at least one spectrum from each group after performing the data grouping, however, minor components can be certainly collected. If minor components are neglected in the extraction of spectra, resultant image data does not reflect the minor components, which means that the quality of the obtained image data becomes low at the cost of high-speed data processing. On the other hand, since, in this embodiment, the size of the data to be processed can be reduced without neglecting minor components, high-speed data processing can be realized without deteriorating the quality of the resultant image data.

The extracted data generation unit 12 generates extracted data by arranging the spectra corresponding to the measurement points extracted from the groups as a matrix (S206). If the total number of measurement points extracted from the groups is denoted by h, the extracted data is an n×h matrix. Here, since h<m, the size of the extracted data is smaller than that of the original data (n×m matrix). Therefore, the speed of processing performed in the subsequent steps can be increased.

The base vector obtaining section 131 performs the second multivariate analysis on the extracted data. More specifically, first, the base vector obtaining section 131 performs the PCA on the n×h matrix of the extracted data to obtain eigenvectors and eigenvalues (S207). Here, since the number of eigenvectors is denoted by k in S202, the calculation may be performed while assuming the number of eigenvectors is k, in order to simplify the calculation.

Next, the base vector obtaining section 131 arranges the obtained k eigenvectors in n dimensions in a k×n matrix and performs the ICA on the k×n matrix (S208).

The ICA is a calculation method for separating a multidimensional signal into a plurality of statistically independent components. If the k×n matrix including the k eigenvectors in the n dimensions obtained a result of the PCA is denoted by Y, a separation matrix W, with which S=WY, is obtained for Y in the ICA according to this embodiment. Here, S denotes a source matrix, which is a k×n matrix in which k source vectors in the n dimensions are arranged. The base vector obtaining section 131 performs convergence calculation while changing the separation matrix W so that the statistical independence of each source vector in the source matrix S becomes maximum. The separation matrix is a k×k matrix in which separation vectors, which are k row vectors in k dimensions, are arranged. By using the separation matrix W obtained in this manner, the source matrix S can be obtained from multidimensional data in which a plurality of signals are superimposed, and the individual signals can be estimated or restored.

Before the ICA is performed, the eigenvectors obtained as a result of the PCA may be whitened, and the calculation process of the ICA may be performed by performing the ICA on the k×n matrix including the whitened k eigenvectors in the n dimensions. The whitening is performed by multiplying each eigenvector obtained as a result of the PCA by the reciprocal of the square root of the corresponding eigenvalue.

Next, the base vector obtaining section 131 calculates the source matrix S by multiplying a transposed matrix of the separation matrix W obtained as a result of the ICA, the matrix L, and the k×n matrix including the whitened eigenvectors. The source vectors included in the source matrix S can be regarded as vectors obtained by reconstructing the eigenvectors obtained as a result of the PCA using the separation vectors obtained as a result of the ICA such that the statistical independence of the each eigenvector becomes maximum. Here, n values included in the source vectors correspond to n score values of independent components. In addition, independent component spectra can be obtained using an inverse matrix of the whitened eigenvectors, a transposed matrix of L, and a transposed matrix of the separation matrix W. Thus, the base vector obtaining section 131 obtains the separation matrix W and sets the first base vectors including the separation matrix W, the matrix L, and the eigenvectors Y to obtain the independent component scores, which are the second score values, and the independent component spectra (S208 and S209).

The image data obtaining section 132 generates the independent component scores at the measurement points and independent component score plots, which are image data indicating the spatial distribution of the independent component scores, on the basis of positional information regarding the measurement points (S210). If the data obtained from the measurement unit 3 or the external storage unit 5 is data in which spectra are stored in accordance with points on an XY plane, the independent component score plots are two-dimensional intensity distribution data. Similarly, if the data obtained from the measurement unit 3 or the external storage unit 5 is data in which spectra are stored in accordance with points in an XYZ space, the independent component score plots are three-dimensional intensity distribution data.

The independent component score plots generated by the image data obtaining section 132 are displayed on the image display unit 4 as images (S211) or stored in the external storage unit 5 (S212) as necessary.

An independent component score plot is obtained for each separation vector in the separation matrix W. The image data obtaining section 132 may add information regarding an arbitrary color to each of an arbitrary number of independent component score plots among the obtained k independent component score plots and create a new independent component score plot by superimposing the arbitrary number of independent component score plots. In doing so, the image display unit 4 can display a false-color image in which different colors are used for different components in the sample.

Alternatively, the image display unit 4 need not display images, but the percentages of the components may be obtained on the basis of the independent component score plots or the independent component scores. At this time, for example, if the percentage of a component unique to a certain tissue such as cancer exceeds a certain value, the image display unit 4 may display an alarm to inform a user of presence of the certain tissue. Alternatively, for example, if it is determined as a result of image processing performed by the data processing apparatus 1 on the independent component score plots that a certain component is distributed in a certain shape, the image display unit 4 may display an alarm to inform the user of the state of the certain component. Alternatively, the image display unit 4 may display the independent component spectra separately from the independent component scores or the independent component score plots. In doing so, the independent component score plots and the corresponding independent component spectra can be compared with each other, thereby making it easier to interpret results.

In this embodiment, the first multivariate analysis is performed on data including a plurality of spectra. A plurality of groups are set for the data using the second base vectors on the basis of results of the first multivariate analysis, and spectra are extracted from the groups. As a result, unlike a case in which spectra are randomly extracted from all the spectra without setting groups, the amount of data can be reduced without neglecting minor components. By performing the second multivariate analysis on the extracted data, which is obtained as a result of the reduction of the amount of data, the amount of calculation and the calculation time to obtain the first base vectors can be reduced without deteriorating the quality of results of the calculation.

Second Embodiment

As a second embodiment, a configuration example in which data including a plurality of spectra is obtained from a sample at least twice will be described with reference to FIG. 1 and FIGS. 3 to 5H.

The configuration of a data processing apparatus according to the second embodiment is the same as that of the data processing apparatus 1 according to the first embodiment.

FIG. 3 is a flowchart illustrating an operation performed by a sample data obtaining system according to this embodiment. In this embodiment, data including a plurality of spectra is obtained twice. Data obtained in a first operation for obtaining data (hereinafter referred to as "pre-scanning") is used for obtaining base vectors through a multivariate analysis. Data obtained in a second operation for obtaining data (hereinafter referred to as "main scanning") is used for obtaining score values using the base vectors obtained from the data obtained through the pre-scanning.

In the pre-scanning, a data set is obtained using a smaller number of measurement points than in the main scanning. That is, by performing the multivariate analysis on the data obtained after reducing the number of measurement points in advance, the time taken to complete the data grouping and the time taken to obtain the base vectors can be reduced. In addition, by obtaining the base vectors from the data obtained through the pre-scanning and sequentially obtaining the score values during the main scanning, images can be sequentially displayed while performing the main scanning.

Before the pre-scanning, the control unit 2 determines a first region, in which the measurement unit 3 measures spectra during the pre-scanning (S301). The measurement unit 3 measures spectra in the determined first region and obtains first data including the obtained spectra (correspond to "first spectra").

As an example of a method for measuring a plurality of spectra at measurement points in the determined region and obtaining data including the plurality of spectra, a case in which the determined region is a two-dimensional region will be described with reference to FIGS. 1 and 4A to 4C.

As a method for performing measurement at the measurement points in the determined region, a method in which the determined region is divided into a plurality of partial subregions and the subregions are sequentially measured is used. Alternatively, measurement may be performed by moving a probe having a one-dimensional shape in a direction perpendicular to an incident direction of the probe.

Figure 4A:
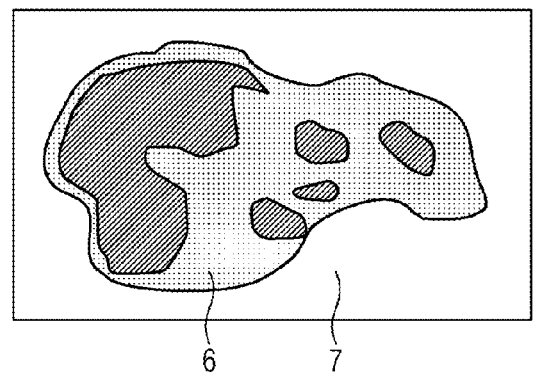
FIGS. 4A to 4C are diagrams illustrating a method for measuring a sample according to the second embodiment.

As a sample 6 in which spectra are measured by the measurement unit 3, a sample fixed on a substrate 7 or a sample sandwiched by two substrates is used. FIG. 4A illustrates the sample 6 fixed on the substrate 7.

Figure 4B:
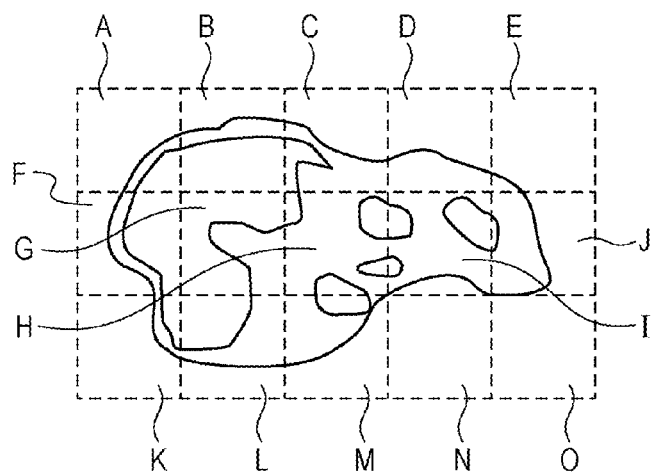

An example of the method in which the determined region is divided into a plurality of partial subregions and the subregions are sequentially measured will be described with reference to FIG. 4B. The determined region is divided into a plurality of partial subregions, namely subregions A to O, and these subregions are sequentially measured. The sizes and shapes of the partial subregions may be arbitrarily determined, but each subregion may correspond to the field of view of the measurement unit 3. In addition, the partial subregions may overlap with one another.

For example, if the measurement unit 3 is a laser scanning measurement apparatus, first, the measurement unit 3 measures a first subregion (for example, the subregion A) through two-dimensional laser scanning. After the measurement in the first subregion is completed, the measurement unit 3 moves the field of view thereof to a second subregion (for example, the subregion B) by moving, using a driving source, which is not illustrated, a sample stage, which is not illustrated, on which the substrate 7, on which the sample 6 is fixed, is mounted. Next, the measurement unit 3 performs measurement in the second subregion through two-dimensional laser scanning. By repeating this procedure and sequentially performing measurement in all the subregions, the measurement unit 3 measures spectra at all the measurement points in the determined region and obtains data including the plurality of spectra.

Here, measurement may be performed a plurality of times in each subregion using laser light having a plurality of wavelengths. In this case, after the measurement is performed in all the subregions using laser light having an arbitrary wavelength, the measurement is performed again in all the subregions using laser light having another arbitrary wavelength. Alternatively, the measurement may be performed a plurality of times at an arbitrary measurement point in the subregions using laser light having a plurality of wavelengths, and then the measurement may be performed at another arbitrary measurement point in the same manner. That is, the measurement may be performed in the subregions using different parameters, and then obtained measurement data may be combined to create data including a plurality of spectra, or spectra may be obtained while changing the parameter at each measurement point in the subregions.

The method for performing measurement in the subregions using one of the parameters at a time is effective if the sample 6 is static and the shape of the sample 6 does not change over time. On the other hand, the method for obtaining spectra while changing the parameter at each measurement point in the subregions is effective if the sample 6 is dynamic and the shape of the sample 6 changes over time.

Next, the method for performing measurement by moving a probe having a one-dimensional shape in a direction perpendicular to a longitudinal direction of the probe will be described with reference to FIG. 4C.

Figure 4C:
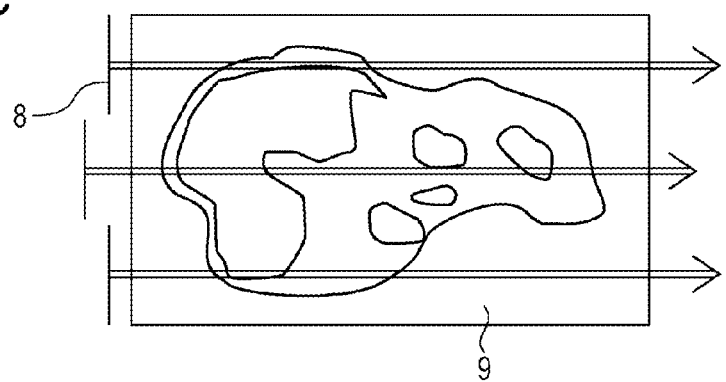

In FIG. 4C, measurement is performed at the measurement points in the determined region by moving a probe 8 in a direction 9. For example, if the measurement unit 3 is a laser scanning measurement apparatus, a laser moved in a one-dimensional direction at high speed may be regarded as the probe 8 having a one-dimensional shape. By moving the sample stage, which is not illustrated, on which the substrate 7, on which the sample 6 is fixed, is mounted relative to the probe 8 using the driving source, which is not illustrated, measurement is performed at the measurement points in the determined region. Compared to the method in which the determined region is divided into a plurality of partial subregions, this method is advantageous in that the configuration of the measurement unit 3 can be simplified.

The first region is at least part of the entirety of the region that can be measured by the measurement unit 3. The first region may be the entirety of the region in which the sample 6 exists, but a region in which an arbitrary number of measurement points are selected from all the measurement points included in the region is the first region. The first region may be set in a range including at least the entirety of the region in which the sample 6 exists. In doing so, even if components and tissues included in the sample 6 are uneven, data that evenly includes the spectrum of each component can be obtained, and therefore the accuracy of separating the components using the separation matrix W obtained in the subsequent processing can be improved.

A method for setting the first region will be described hereinafter while assuming that the measurement at the measurement points in the determined region is performed using the method in which the determined region is divided into a plurality of partial subregions and the subregions are sequentially measured. In this case, a selection pattern of the measurement points for each partial subregion is set, and the first region can be set by applying the pattern to all the partial subregions. FIGS. 5A to 5H illustrate selection patterns of the measurement points that can be set for the partial subregions. Measurement points indicated by hatched squares illustrated in FIGS. 5A to 5H are selected.

Figure 5A:
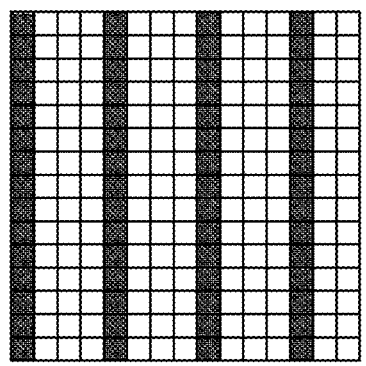
FIGS. 5A to 5H are diagrams illustrating selection patterns of measurement points according to the second embodiment.
Figure 5B:
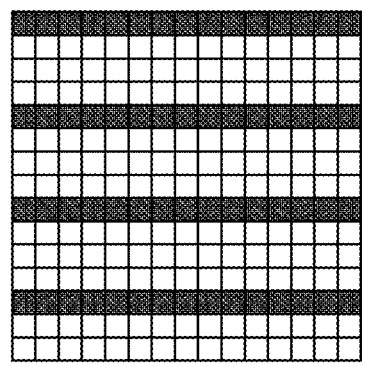
Figure 5C:
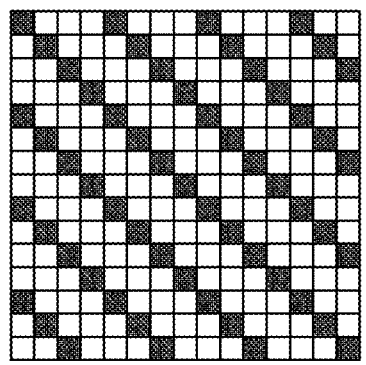
Figure 5D:
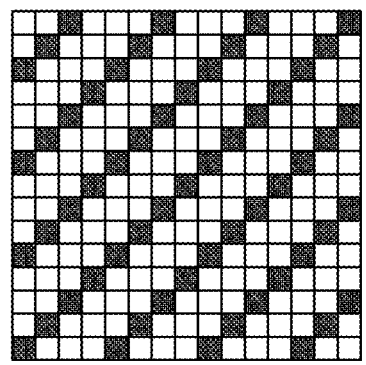
Figure 5E:
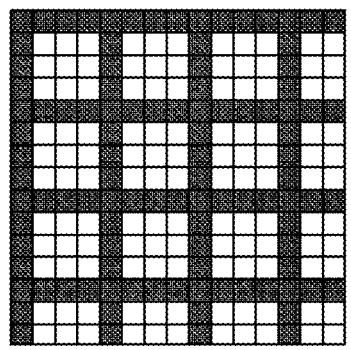
Figure 5F:
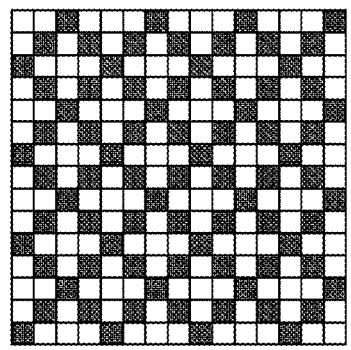
Figure 5G:
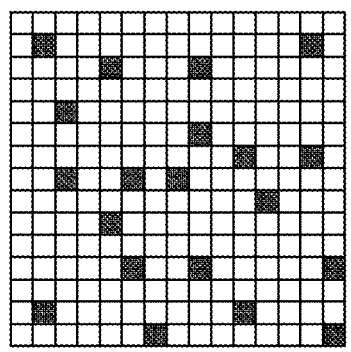
Figure 5H:
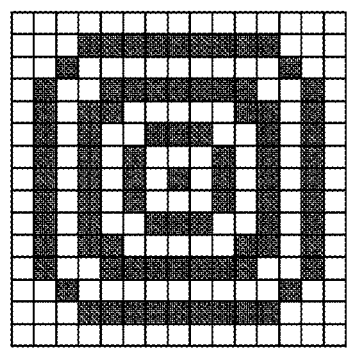

The selection patterns of the measurement points include patterns in which measurement points are arranged in a one-dimensional direction (FIGS. 5A to 5D) and patterns in which a plurality of patterns in which measurement points are arranged in a one-dimensional direction are combined (FIGS. 5E and 5F). The selection pattern of the measurement points may be a pattern in which measurement points are randomly distributed (FIG. 5G) or a pattern in which measurement points are concentrically distributed around the center of the field of view (FIG. 5H).

If a pattern in which measurement points are arranged in a one-dimensional direction is adopted as the selection pattern of the measurement points, the configurations of the control unit 2 and the measurement unit 3 can be simplified.

If a pattern in which measurement points are arranged in a two-dimensional direction is adopted as the selection pattern of the measurement points, the configurations of the control unit 2 and the measurement unit 3 become complex, but a certain component of the sample can be measured even if the certain component of the sample is distributed in a one-dimensional direction.

If a pattern in which measurement points are randomly distributed is adopted as the selection pattern of the measurement points, the number of measurement points can be efficiently reduced compared to when one of the above-described patterns is adopted.

If a pattern in which measurement points are concentrically distributed around the center of the field of view as the selection pattern of the measurement points, a decrease in signal intensity due to the measurement method used by the measurement unit 3 can be compensated. For example, if a laser scanning measurement apparatus is used as the measurement unit 3, the amount of laser light radiated differs between the center of the field of view and the periphery of the field of view depending on the type of objective lens used, and accordingly signal intensity measured in the periphery of the field of view might decrease. If the signal intensity decreases, variation in the spectra included in the data obtained as a result of the pre-scanning becomes large.

Therefore, as illustrated in FIG. 5H, the measurement points may be set in such a way as to obtain data at the center of the field of view.

Next, the data processing apparatus 1 obtains the first data (S302). As in the first embodiment, the data processing apparatus 1 performs the data grouping on the first data, and then selects at least one spectrum from each group and generates extracted data including the selected spectra. Next, the data processing apparatus 1 performs the PCA and the ICA on the extracted data to obtain eigenvectors Y, eigenvalues, a separation matrix W, and the matrix L. The data processing apparatus 1 stores the obtained eigenvectors Y, eigenvalues, and the separation matrix W, and the matrix L in the internal storage unit 14 (S303 to S309).

Before the main scanning, the control unit 2 determines a second region, in which the measurement unit 3 measures spectra during the main scanning (S310). The measurement unit 3 measures spectra in the determined second region and obtains second data including the obtained spectra (correspond to "second spectra").

The second region is at least part of the entirety of the region that can be measured by the measurement unit 3 and a region including a larger number of measurement points than the first region. The second region may be the entirety of the region in which the sample 6 exists, but may be a region in which an arbitrary number of measurement points are selected from all the measurement points included in the entirety of the region in which the sample 6 exists, insofar as the region includes a larger number of measurement points than the first region.

The second region may be set in a range included in the range in which the data processing apparatus 1 has been set, but may be set in a range including a range outside the range in which the first region has been set. Alternatively, the range in which the first region has been set and the range in which the second region is set need not overlap and may be separated from each other.

Alternatively, the second region need not be determined after the first region is determined, but the second region may be determined first, and then the first region may be determined on the basis of a range in which the second region has been set. More specifically, after the user determines the second region, the first region may be set in a range that at least includes a range in which the second region has been set. In doing so, if a range of the sample 6 to be observed is known in advance, the measurement of spectra to the processing of data can be performed at higher speed.

The data processing apparatus 1 obtains the second data (S311). The data processing apparatus 1 obtains independent component scores of the second data using the first base vectors including the eigenvectors Y, the eigenvalues, the separation matrix W, and the matrix L read from the internal storage unit 14 (S312).

As in the first embodiment, the analysis unit 13 obtains the independent component scores at the measurement points using the first base vectors obtained as a result of the pre-scanning and the spectra at the measurement points obtained as a result of the main scanning. The image data obtaining section 132 generates independent component score plots on the basis of the obtained independent component scores and positional information regarding the measurement points (S313). As in the first embodiment, the independent component score plots generated by the image data obtaining section 132 are displayed on the image display unit 4 as images (S314) or stored in the external storage unit 5 (S315) as necessary.

Here, in the measurement performed at the measurement points in the second region, first, the second region is divided into a plurality of partial subregions. The measurement is then performed using the method in which the subregions are sequentially measured. Data is obtained as a plurality of pieces of data divided in accordance with the subregions. Since the pieces of data are sequentially obtained, a piece of data may be obtained from a certain subregion, and, after the measurement unit 3 moves to a next subregion for measurement, the processing in S312 to S315 may be performed using the already obtained piece of data. In doing so, images may be sequentially displayed for the subregions. That is, according to this embodiment, base vectors are obtained in advance by performing the pre-scanning, and image data is sequentially generated for the subregions using the base vectors, thereby enabling the user to sequentially obtain information before the measurement of the sample is fully completed.

Other Embodiments

Although the embodiments of the present invention have been described above, the present invention is not limited to these embodiments, and may be modified or altered in various ways without deviating the scope thereof.

The present invention may be implemented as a system, an apparatus, a method, a program, a storage medium, or the like. In addition, in the above description, the present invention is applied to the sample data obtaining system including the data processing apparatus 1, the reception processing unit 20, the image display unit 4, and the external storage unit 5. The present invention, however, may be applied to a system including a combination of a plurality of other devices or may be applied to an apparatus including a single device. For example, the present invention may be applied to a data display system including the data processing apparatus 1 and the image display unit 4.

In addition, in a system including a combination of a plurality of devices to which the present invention is applied, some or all of the devices may be connected to one another by a network including the Internet. For example, the system may transmit obtained data to a server connected to the network. The server may perform the processing in the present invention, and then the system may receive obtained results from the server and, for example, display images.

The present invention includes a case in which the functions according to each of the above-described embodiments are realized by directly or remotely supplying a software program to a system or an apparatus and reading and executing a supplied program code using a computer of the system or the apparatus. In this case, the supplied program is a computer program corresponding to one of the flowcharts illustrated in the drawings in the above-described embodiments. Therefore, the program code installed on the computer in order to realize the functions and the processing in the present invention using the computer also realizes the present invention.

That is, the present invention includes the computer program for realizing the functions and the processing in the present invention. In this case, the computer program may be an object code, a program executed by an interpreter, script data supplied to an operating system (OS), or the like insofar as the object code, the program executed an interpreter, the script data, or the like has a function of the program.

A computer-readable storage medium for supplying a computer program may be, for example, a hard disk, an optical disk, a magneto-optical (MO) disk, a compact-disc read-only memory (CD-ROM), a compact disc-recordable (CD-R), a compact disc-rewritable (CD-RW), a magnetic tape, or the like. Alternatively, the computer-readable storage medium may be a nonvolatile memory card, a read-only memory (ROM), a digital versatile disc (DVD) (DVD-ROM or DVD-R), or the like.

Alternatively, the program may be supplied by connecting to a website on the Internet using a browser of a client computer and downloading the computer program in the present invention from the website to a storage medium such as a hard disk. In this case, the program to be downloaded may be a compressed file having an automatic installation function. In addition, the present invention also includes a World Wide Web (WWW) server that enables a plurality of users to download a program file for realizing the functions and the processing in the present invention using a computer.

First Example

An example in which data obtained from biological samples using an SRS microscope, which is an apparatus that uses SRS, was analyzed will be described.

As the biological samples, pancreas tissues and liver tissues of a mouse, each of which includes a tumor portion and a non-tumor portion, subjected to a formalin fixation process were used.

Raman spectra were measured in two-dimensional regions of the biological samples. Each measurement region was 240 micrometers in a vertical direction and 480 micrometers in a horizontal direction and included 1,500 pixels in the vertical direction and the 4,000 pixels in the horizontal direction. A region of Raman shifts of 2,800 to 3,100 cm$^{-1}$ was equally divided into 91 stages, and Raman intensity was measured at each wavenumber.

In the analysis, two-dimensional observation data regarding the tissues collected as a single piece of data was used. In the measurement, the entirety of the measurement region was divided into a plurality of subregions (tiles) and measured, and then data regarding the entirety of the measurement region was obtained by connecting the tiles. Since the tiles overlapped with one another, spectra of the overlap regions were removed before the tiles were connected. The number of dimensions of the obtained data was 91, and the number of measurement points was 5,720,000.

At the beginning of the analysis, the data grouping was performed on the data. First, eigenvectors and eigenvalues were obtained by performing the PCA on the data. Because there were three eigenvectors whose eigenvalues had contribution percentages of 1% or more, these three eigenvectors were selected and used as the second base vectors.

Inner products between the eigenvectors and spectra included in the data were calculated to obtain principal component scores. FIGS. 6A to 6E illustrate the eigenvectors and two-dimensional plots of the principal component scores. The horizontal axes for the eigenvectors illustrated in FIGS. 6A and 6B correspond to Raman shifts. The two-dimensional images of the principal component scores illustrated in FIGS. 6C to 6E were generated by plotting the two-dimensional intensity distribution of the principal component scores.

Figure 6A:
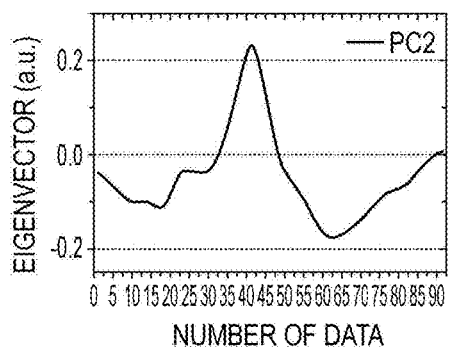
FIGS. 6A to 6E are diagrams illustrating two-dimensional intensity distribution images of eigenvectors and principal component scores in a first example.
Figure 6B:
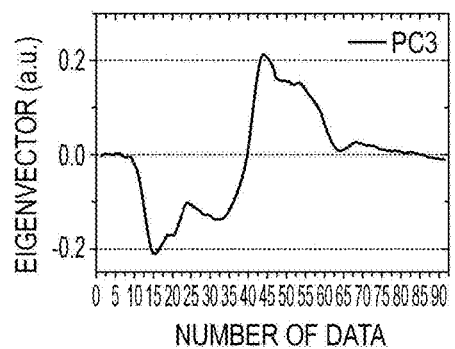
Figure 6C:
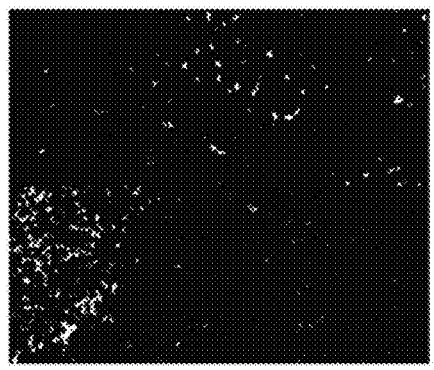
Figure 6D:
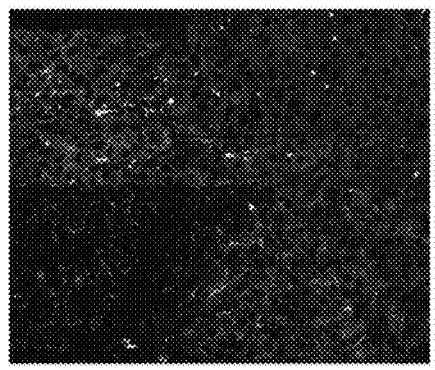
Figure 6E:
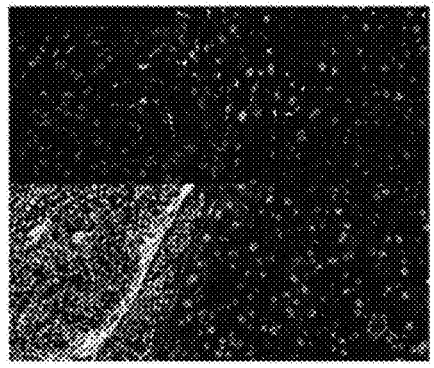

Next, by comparing the two-dimensional images of the principal component scores illustrated in FIGS. 6C to 6E with images obtained by staining biological samples including similar tissues and observing the biological samples, components indicated by the principal component scores were identified. As a result, it could be seen from FIG. 6C that in a data group (hereinafter referred to as "PC2−") that had been obtained using the second eigenvector (FIG. 6A) and whose principal component scores were smaller than 0, blood cells could be extracted and imaged as feature values. In addition, it could be seen from FIG. 6D that in a data group (hereinafter referred to as "PC3−") that had been obtained using the third eigenvector (FIG. 6B) and whose score values were smaller than 0, cytoplasm and fat droplets could be extracted and imaged. Furthermore, it could be seen from FIG. 6E that in a data group (hereinafter referred to as "PC3+") that had been obtained using the third eigenvector (FIG. 6B) and whose score values were equal to or larger than 0, cell nuclei, fiber, and blood cells could be extracted and imaged.

Next, the data groups were compared with one another to identify a feature value that was observed in a plurality of data groups. As a result, blood cells were identified in two data groups. More specifically, blood cells were classified into both PC2− and PC3+.

In order to remove an overlap of components between the two different data groups and set the same number of measurement points for each component in subsequent data extraction, one of the two data groups was subtracted from the other to create a new data group. On the basis of these results, data groups were set for the data. More specifically, data groups were set for the data by setting PC2− as Group 1, PC3− as Group 2, and a data group obtained by subtracting PC2− from PC3+ as Group 3. Group 1 represented blood cells, Group 2 represented cytoplasm and fat droplets, and Group 3 represented cell nuclei and fiber.

Next, an arbitrary number of spectra were extracted from the spectra included in each of Group 1, Group 2, and Group 3. The extraction of data was performed such that the number of spectra extracted from each of the data groups became the same. More specifically, the data was extracted such that the number of spectra extracted from each of the data groups became 1,000, 3,500, 10,000, 20,000, or 40,000, and extracted data was created. The extraction of data was randomly performed for each of the data groups. Data reduction ratios, which were ratios of the number of spectra reduced as a result of the extraction to the total number of spectra, were 99.95%, 99.72%, 99.5%, 99.0%, and 97.9%, respectively, which meant that the size of the data was significantly reduced.

Next, the PCA and the ICA, the second multivariate analyses, were performed on the extracted data.

First, eigenvectors obtained as a result of the PCA will be described. In order to examine the effect of the data grouping, the eigenvectors obtained in this example and eigenvectors obtained by performing the PCA on an extracted data set generated by randomly extracting data from all the measurement points without setting data groups were compared. More specifically, a procedure from extraction of data to obtaining of eigenvectors through the PCA was performed five times for the data for which the data groups had been set, in order to examine variation in the eigenvectors in each trial. The variation were evaluated using Expression (1), where differences between the eigenvectors obtained in each trial and an average of the eigenvectors obtained in all the trials was evaluated. Here, i denotes the number of trials, j denotes the number of dimensions of data, and $X_{ave}$ denotes the average of the five trials at a certain number of dimensions of data j.

$$\alpha = \sum_{j=1}^{91} \frac{1}{n} \sum_{i=1}^{5} (X_{ij} - X_{ave})^2 \quad (1)$$

FIG. 7 illustrates a correlation between the variation in the eigenvectors and the data reduction ratio. A displacement value α of the eigenvectors at each data reduction ratio was calculated for both the case in which the data grouping was performed and the case in which the data grouping was not performed. It could be seen that the variation in the eigenvectors became larger as the amount of data size reduced became larger regardless of whether the data grouping was performed. In addition, it could be seen that compared to the case in which the data grouping was not performed, the variation in the eigenvectors was significantly suppressed when the data grouping was performed. It could be seen from these results that the reproducibility of eigenvectors obtained from extracted data could be improved by reducing the amount of data in accordance with each of the data groups and extracting spectra. That is, it could be seen that by performing the data grouping and extracting data for each of the data groups, the size of data could be efficiently reduced while maintaining the reproducibility of the eigenvectors of the extracted data.

Next, independent component spectra obtained as a result of the ICA will be described. As with the eigenvectors obtained as a result of the PCA, the independent component spectra was calculated five times for each of the case in which the data grouping was performed and the case in which the data grouping was not performed, and variation in the independent component spectra in each trial was examined.

Figure 8A:
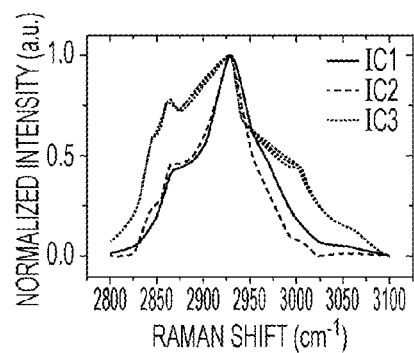
FIGS. 8A to 8H are diagrams illustrating independent component spectra and standard deviations in the first example.
Figure 8B:
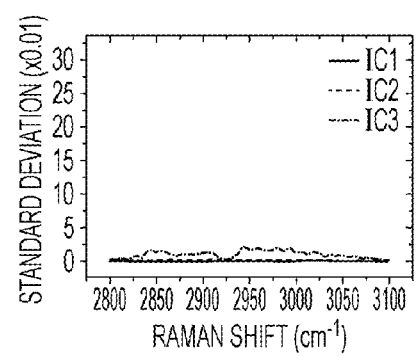
Figure 8C:
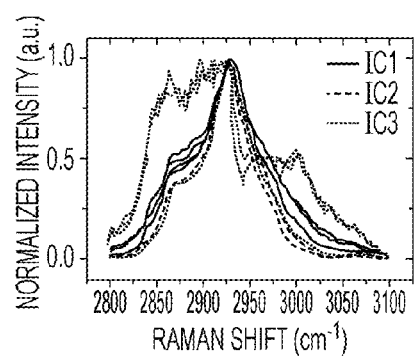
Figure 8D:
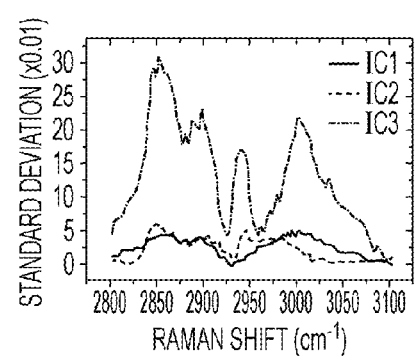
Figure 8E:
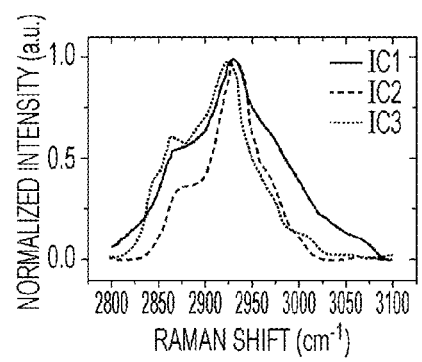
Figure 8F:
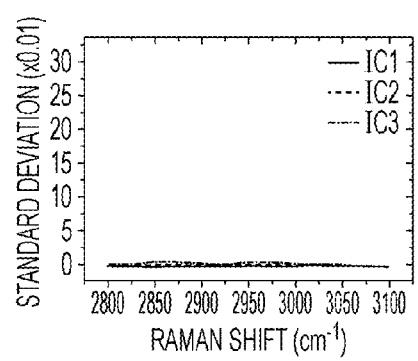
Figure 8G:
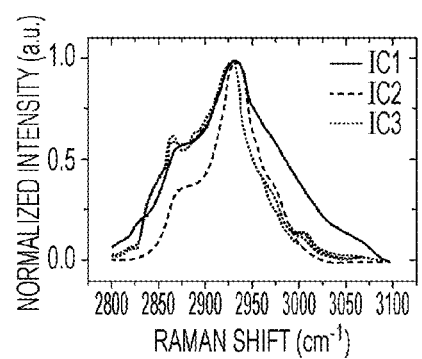
Figure 8H:
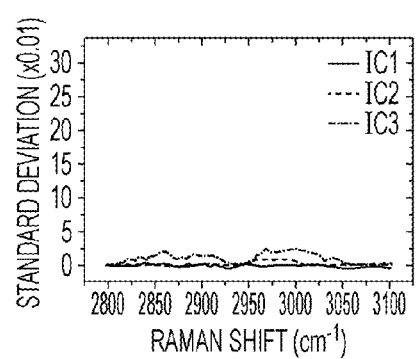

FIGS. 8A to 8H illustrate independent component spectra and standard deviations at a time when the data reduction ratio is 99.0% or 99.95%. FIGS. 8A and 8B illustrate independent component spectra and standard deviations at a time when the grouping was not performed and the data reduction ratio was 99.0%. FIGS. 8C and 8D illustrate independent component spectra and standard deviations at a time when the grouping was not performed and the data reduction ratio was 99.95%. FIGS. 8E and 8F illustrate independent component spectra and standard deviations at a time when the data grouping was performed and the data reduction ratio was 99.0%. FIGS. 8G and 8H illustrate independent component spectra and standard deviations at a time when the data grouping was performed and the data reduction ratio was 99.95%.

In FIGS. 8A to 8H, the horizontal axes represent the Raman shift wavenumber, which corresponds to the number of dimensions of the data (91 dimensions). The variation in the independent component spectra in each of the five trials can be evaluated on the basis of the standard deviation.

When the data reduction ratio was 99.0%, the variation in the independent component spectra in the five trials was suppressed in both the case in which the data grouping was performed and the case in which the data grouping was not performed. When the data reduction ratio was 99.95% and the data grouping was not performed, results varied largely (FIG. 8D) and the data reproducibility is low (FIG. 8C). On the other hand, in the case in which the data grouping was performed, the reproducibility of the independent component spectra was high (FIGS. 8G and 8H) and the reproducibility of the independent component score plots, which corresponded to the independent component spectra as described later, was also significantly high.

In addition, it could be seen that the obtained independent component spectra differed depending on whether the data grouping was performed. This indicates that when the data grouping is performed, minor components can be extracted as main components (principal components) through the multivariate analysis because the number of spectra derived from the minor components and the number of spectra derived from major components are the same. When the data grouping is not performed, spectra are randomly extracted from all the spectra included in the data set. Therefore, the possibility that the spectra derived from the minor components are selected decreases, and accordingly the number of spectra derived from the minor components included in the extracted data decreases, thereby making it difficult to extract the minor components as main components (principal components). As described later, it could be seen that when the data grouping was performed, high component separation capabilities were observed in the independent component score plots.

Figure 9A:
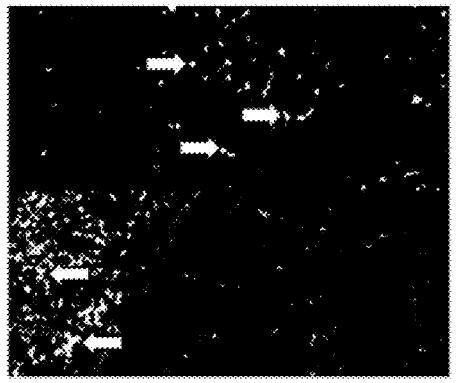
FIGS. 9A to 9F illustrate two-dimensional intensity distribution images of the independent component spectra in the first example.
Figure 9D:
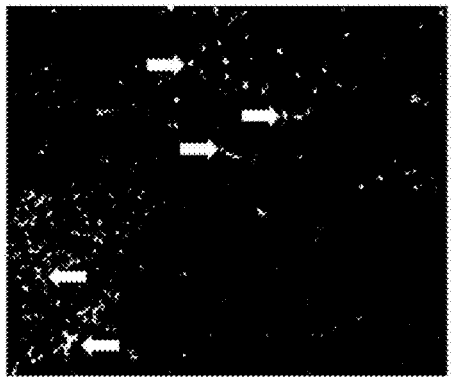
Figure 9B:
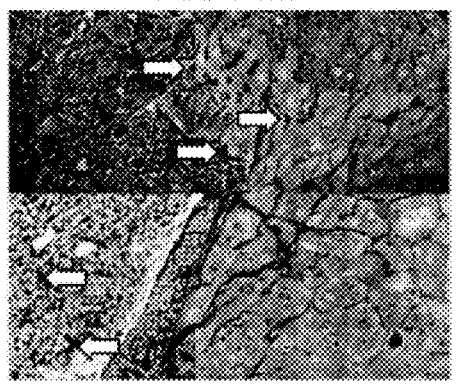
Figure 9E:
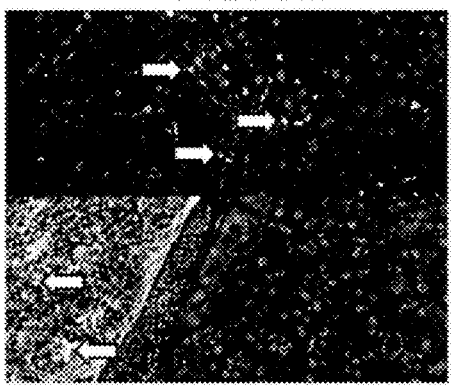
Figure 9C:
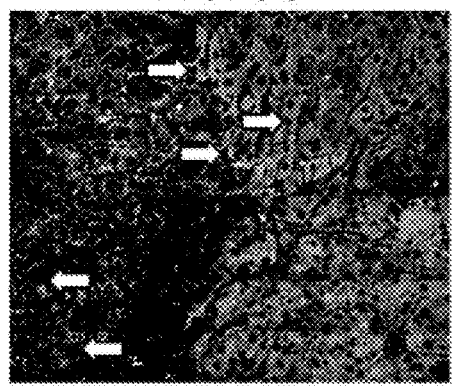
Figure 9F:
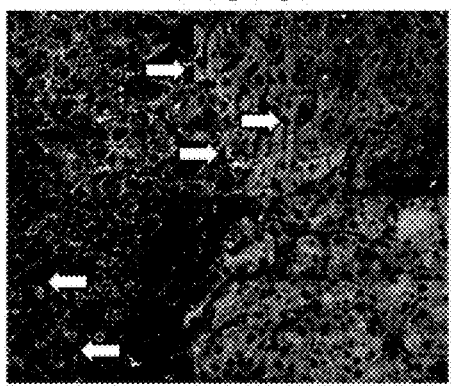

Next, the independent component scores were obtained, and the independent component score plots were displayed as two-dimensional images. FIGS. 9A to 9F illustrate the two-dimensional intensity distribution images of the independent component scores. FIGS. 9A to 9C illustrate independent component score plots obtained when the data grouping was performed and the data reduction ratio was 99.95%. FIGS. 9D to 9F illustrate independent component score plots obtained when the data grouping was not performed and the data reduction ratio was 99.0%.

Portions indicated by arrows illustrated in FIGS. 9A to 9F are portions in which the blood cell component, which is a minor component, is located. When the data grouping was performed, the blood cell component was seen only in FIG. 9A, which indicated that the blood cell component could be clearly separated as an individual component. When the data grouping was not performed, however, the blood cell component was seen in FIGS. 9D and 9E, which indicated that the separation of the minor component was insufficient.

When the data grouping was performed, there was no significant difference between the images of the data reduction ratios of 99.95%, 99.5%, 99.0%, and 97.9%. Therefore, it could be seen that as a result of the data grouping and the extraction of data for each data group, the adverse effect of an increase in the amount of data reduced upon the score plots could be suppressed.

Figure 10:
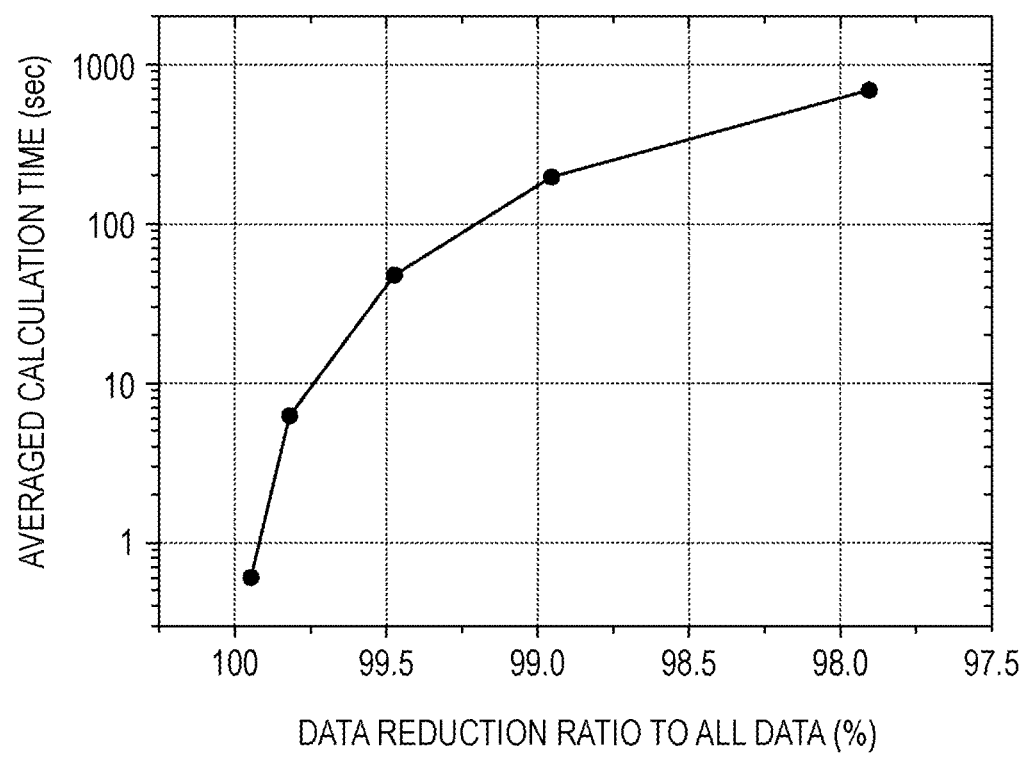
FIG. 10 is a diagram illustrating a correlation between total calculation time taken to complete a PCA and an ICA and the data reduction ratio in the first example.
Figure 12A:
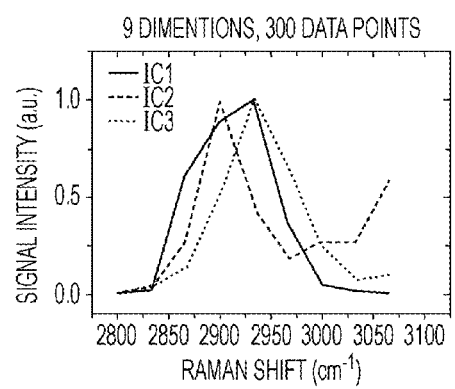
FIGS. 12A to 12D are diagrams illustrating independent component spectra in the second example.
Figure 12B:
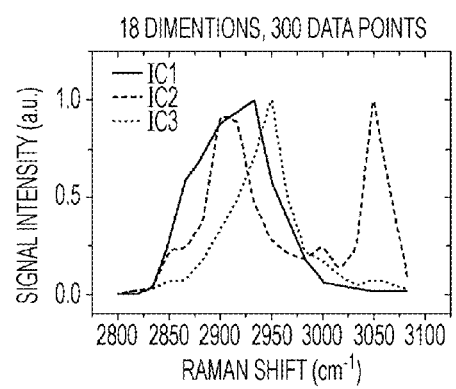
Figure 12C:
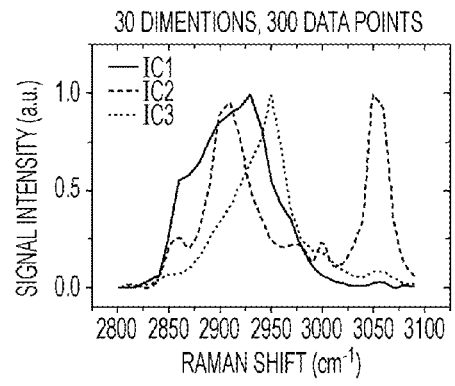
Figure 12D:
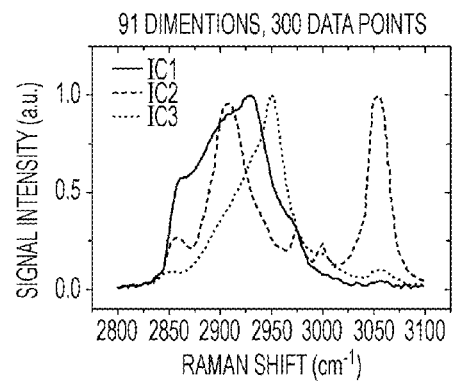

Next, the effect of reducing the calculation time as a result of the reduction of data will be described. FIG. 10 illustrates a correlation between the sum (total calculation time) of the time taken to calculate the eigenvectors through the PCA and the time taken to calculate the separation matrix through the ICA and the data reduction ratio. It could be seen from results that the calculation time could be significantly reduced as a result of the reduction of the amount of data. More specifically, the calculation was completed in 195 seconds at the data reduction ratio of 98.96% and 0.591 second at 99.95%. Since the matrix calculation is performed in the PCA, the amount of calculation increases in proportion to the number of measurement points (the number of spectra). On the other hand, since the convergence calculation is performed in the ICA, the amount of calculation exponentially increases relative to the number of measurement points (the number of spectra). Therefore, it could be seen that by significantly decreasing the number of measurement points, the calculation time could be significantly reduced.

Although experiments relating to Raman spectra have been described in this example, the present invention is not limited to this. For example, the present invention may be applied to another type of spectra such as mass spectra.

Second Example

An example in which a data set obtained from a mixture of three types of polymer beads was analyzed using an SRS microscope will be described.

The materials of the three types of polymer beads were polyurethane, polystyrene, and polymethylmethacrylate. These materials are known to produce different Raman spectra.

As in the first example, Raman spectra were measured in a two-dimensional region of the mixture (sample). The measurement region included 512 pixels in a vertical direction and 512 pixels in a horizontal direction. Other measurement conditions were the same as those in the first example.

The PCA, the first multivariate analysis, was performed on data obtained in this manner to obtain eigenvectors, the second base vectors, and eigenvalues. Since the mixture of the three types of polymer beads was used as a sample in this example, the number of components was 3. Therefore, the number of eigenvectors was set to 3. As in the first example, principal component scores of the obtained eigenvectors were calculated, and two-dimensional images of the principal component scores were obtained. At this time, by normalizing the values of the principal component scores to values within a range of 0 to 255, 8-bit monochrome two-dimensional images of the principal component scores were obtained.

As a result, it could be seen that data groups of principal component scores of PC2−, PC2+, and PC3− had extracted the polymer beads as feature values and imaged the feature values. Here, PC2− indicated a data group that was obtained using a second eigenvector and whose score values are smaller than 0. PC2+ indicated a data group that was obtained using the second eigenvector and whose score values were equal to or larger than 0. PC3− indicated a data group that was obtained using a third eigenvector and whose score values were smaller than 0. The polymer beads were identified by comparing Raman spectra obtained from the polymer beads in the images and Raman spectra of the individual polymer beads.

Next, a threshold was set for each data group of the normalized principle component scores, and data including principal component scores equal to or larger than each threshold was selected. More specifically, a threshold of 98 was set for PC2−, a threshold of 129 was set for PC2+, and a threshold of 112 was set for PC3−. As a result, a new Data Group A including 17,651 pieces of data was generated from the PC2− data group, a new Data Group B including 17,833 pieces of data was generated from the PC2+ data group, and a new Data Group C including 18,750 pieces of data was generated from the PC3− data group.

Next, data was extracted from the data groups (A to C). More specifically, 100 pieces of data were randomly extracted from each of the data groups (A to C). A data set including a total of 300 pieces of data was generated by combining the extracted data. The data reduction ratio of the obtained data set to the original data (262,144 pieces of data) was 99.89%.

The following data sets having different numbers of dimensions of spectrum data were generated for the obtained data.

1) Data Set 1: 9 dimensions (that is, a data set obtained by extracting only Raman intensity whose Raman shift was $2,800+33.3i$ ($cm^{-1}$) (i=0 to 8))
2) Data Set 2: 18 dimensions (that is, a data set obtained by extracting only Raman intensity whose Raman shift was $2,800+16.5i$ ($cm^{-1}$) (i=0 to 17))
3) Data Set 3: 30 dimensions (that is, a data set obtained by extracting only Raman intensity whose Raman shift was $2,800+9.9i$ ($cm^{-1}$) (i=0 to 29))
4) Data Set 4: 91 dimensions (that is, a data set obtained by extracting only Raman intensity whose Raman shift was $2,800+3.3i$ ($cm^{-1}$) (i=0 to 90))

Here, the number of dimensions of Data Set 4 is the largest, and the number of dimensions becomes smaller in Data Set 3, Data Set 2, and Data Set 1 in this order. In this example, Data Set 1, Data Set 2, Data Set 3 were generated by extracting Raman intensity of certain Raman shifts from Data Set 4. More specifically, Data Set 1, Data Set 2, and Data Set 3 were obtained by extracting 9, 18, and 30 different Raman shifts, respectively, from the data regarding 91 different Raman shifts included in Data Set 4. FIG. 11 illustrates a list of Raman shifts included in the data sets. Solid circles in the list illustrated in FIG. 11 indicate Raman shifts extracted in each of the data sets. Because the amount of data included in the data sets is proportionate to the number of dimensions, the amount of data included in Data Set 4 could be reduced in Data Set 1, Data Set 2, and Data Set 3 by about 90%, 80%, and 67%, respectively.

In this example, by decreasing the number of dimensions of an obtained data set and reducing the size of the data set, the time taken to complete the analysis, which will be described later, can be reduced. If, however, a data set is obtained as a result of measurement after the number of dimensions is decreased, that is, for example, if only certain Raman spectra are measured, not only the time taken to complete the analysis but also the time taken to complete the measurement can be reduced.

Next, the PCA and the ICA, the second multivariate analyses, were performed on the data sets to obtain independent component spectra and distribution images of independent component scores using the first base vectors. FIGS. 12A to 12D illustrate the independent component spectra obtained from the data sets. FIGS. 12A to 12D illustrate the independent component spectra obtained from Data Set 1, Data Set 2, Data Set 3, and Data Set 4, respectively. It can be seen that the independent component spectra obtained from Data Set 4 indicate spectrum information the most precisely. On the other hand, it can be seen that as the number of dimensions of the data set decreases, precise information regarding the spectra held by the original data set is lost more.

Figure 13:
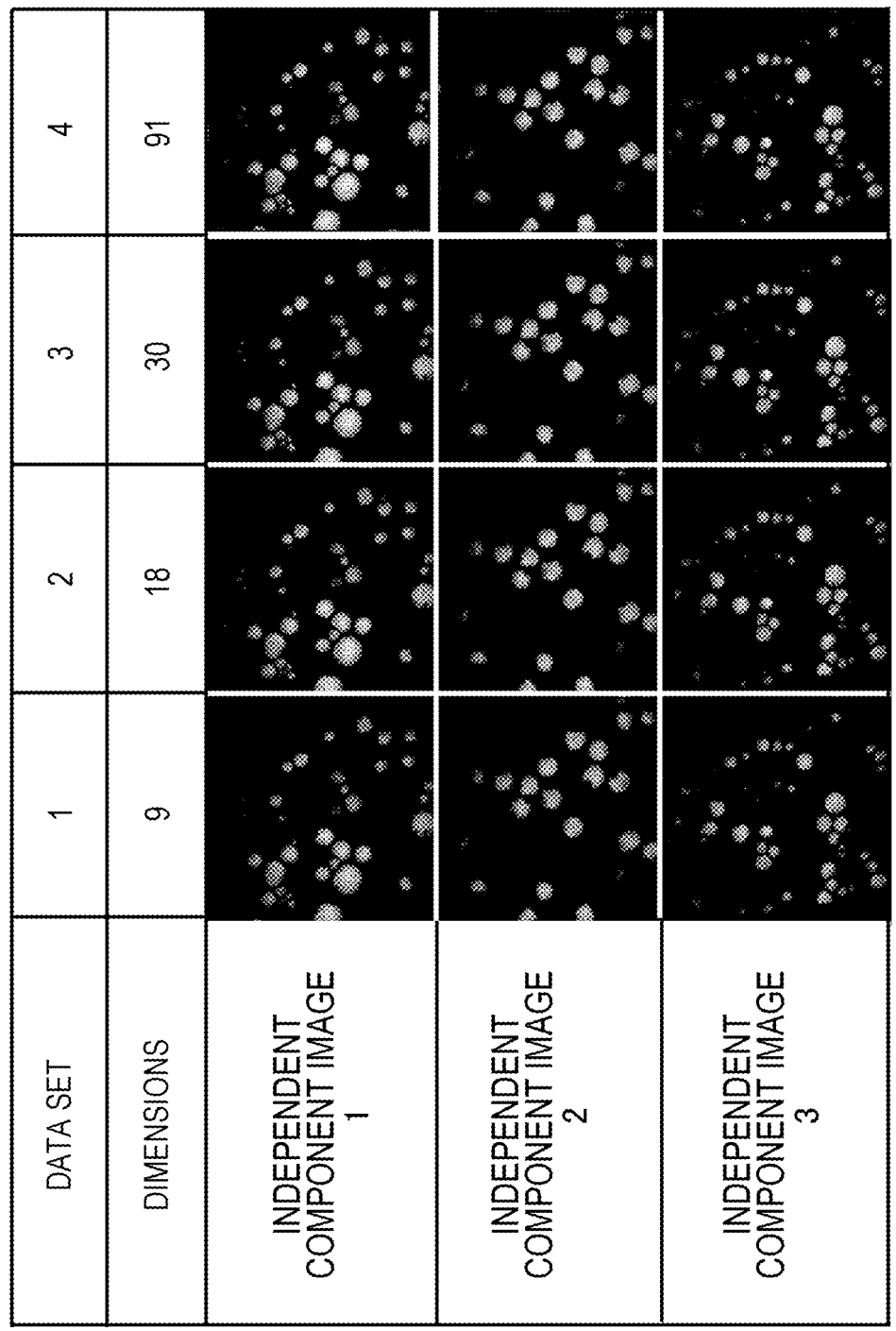
FIG. 13 illustrates two-dimensional intensity distribution images of the independent component spectra in the second example.

FIG. 13 illustrates the distribution images (independent component images) of the independent component scores obtained from the data sets. As a result of a comparison between the distribution images of the independent component scores, it could be seen that all the distribution images of the independent component scores generated from the data sets indicated the distribution of the three different types of polymer beads. By comparing the distribution images of the independent component scores generated from the data sets with one another in detail, it could be seen that as the number of dimensions reduced became larger, slight noise in the image increased. Significant deterioration in image quality, however, was not observed in the displayed distribution of the polymer beads. That is, it could be seen that although information regarding the independent component spectra obtained from a data set became coarser as the number of dimensions of the data set decreased, the distribution image of the independent component scores did not substantially change.

By examining distribution images of principal component scores, it could be seen that the distribution of the polymer beads could be imaged even by the distribution images of the principal component scores obtained from a data set whose number of dimensions had been reduced. Furthermore, it could be seen that if the number of pieces of data in a data set was decreased to 30 (a reduction ratio of 99.99% of the total number of pieces of measurement data), the same distribution images of the independent component scores as those illustrated in FIG. 13 and the distribution images of the principal component scores could be obtained.

As a result of the above-described experiments, it could be seen that even if the size of a data set was reduced by decreasing the number of dimensions of the data set, no significant difference was caused between the resultant distribution images of the components obtained after the above-described analysis.

Furthermore, it could be seen that by calculating the score values of a data set using first base vectors obtained for a data set that had been obtained at other measurement positions and whose number of dimensions had been reduced, the distribution of the three types of polymer beads could be displayed. At this time, the number of dimensions of the former data set was the same as the number of dimensions of the data set used for obtaining the base vectors. That is, it could be seen that this example could be applied not only to data sets obtained at the same measurement position but also to data sets obtained at different measurement positions.

If this example is applied to data sets obtained at different measurement positions, only part of the wavenumber (dimensions) is extracted from a data set of a broad region obtained from a sample as a result of pre-scanning to decrease the number of dimensions, and then base vectors may be obtained. By using this method, spectrum information included in the data set can be selected, and base vectors of the selected spectrum information can be obtained. By using the base vectors obtained in this manner, intensity distribution information having a plurality of score values can be obtained for each piece of the selected spectrum information. The selection of the spectrum information is effective especially in an analysis of a data set obtained from a sample including various components.

The reduction of the number of dimensions of a data set by selecting the wavenumber can reduce not only the time taken to complete the analysis but also the time taken to complete the measurement. This is effective especially when the time taken to obtain a data set is longer than the time taken to complete the analysis of the data set.

As an example, the time taken to complete the measurement and the time taken to complete the analysis when a high-speed Raman spectrum data obtaining system (Y. Ozeki et al. Nature Photonics vol. 6, pp. 845-851, 2012) was used were measured. As a result, whereas the time taken to obtain (measure) the data was 33.3×n (milliseconds), the time taken to calculate the data was 1.21×n (milliseconds). Here, n denotes the number of Raman shifts (the number of dimensions) of Raman spectra included in the obtained data set. The measurement was performed in a two-dimensional region including 512 pixels in a vertical direction and 512 pixels in a horizontal direction, and the number of principal components was 3. That is, in this system, the time taken to obtain the data was approximately 33 times longer than the time taken to calculate the data. Thus, when the time taken to complete the measurement is longer than the time taken to complete the analysis, the time taken to display images since the beginning of the measurement can be reduced by performing the measurement while reducing the number of dimensions. Accordingly, the intensity distribution data can be displayed rapidly.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-260678 filed Dec. 17, 2013 and No. 2014-210283 filed Oct. 14, 2014, which are hereby incorporated by reference herein in their entirety.

What is claimed is:

1. A data processing apparatus for processing data including a plurality of spectra, comprising:
   a processor; and
   a memory,
   wherein the processor receives the data including the plurality of spectra and stores the data in the memory,
   wherein the processor performs a first multivariate analysis on the data stored in the memory to obtain a plurality of second base vectors,
   wherein the processor classifies the plurality of spectra included in the data stored in the memory into a plurality of groups based on score values obtained from each of the plurality of spectra and each of the plurality of second base vectors;
   wherein the processor generates extracted data by extracting a part of the plurality of spectra from each of the plurality of groups, wherein a size of the extracted data is smaller than that of the data stored in the memory;
   wherein the processor performs a second multivariate analysis on the extracted data to obtain a plurality of first base vectors from the extracted data,
   wherein the first multivariate analysis at least includes a principal component analysis, and
   wherein the second multivariate analysis includes at least both a principal component analysis and an independent component analysis.

2. The data processing apparatus according to claim 1, wherein the processor attributes the plurality of spectra included in the data stored in the memory or a plurality of spectra different from the plurality of spectra included in the data stored in the memory to a plurality of components using the plurality of first base vectors to generate image data indicating distribution of a portion of the plurality of components.

3. The data processing apparatus according to claim 2, wherein the image data is two-dimensional or three-dimensional intensity distribution data regarding score values, which are inner products between the plurality of spectra and the portion of the plurality of first base vectors.

4. A data display system comprising:
   the data processing apparatus according to claim 2; and
   a display configured to display the image data as an image.

5. The data processing apparatus according to claim 1, wherein a calculation amount of the second multivariate analysis for a unit amount of data is smaller than a calculation amount of the first multivariate analysis for a unit amount of data.

6. The data processing apparatus according to claim 1, wherein the plurality of spectra include at least any of spectroscopy spectra in an ultraviolet range, a visible range, or an infrared range, Raman spectra, and mass spectra.

7. The data processing apparatus according to claim 1, wherein the data includes data storing the portion of the plurality of spectra corresponding to points on an XY plane.

8. The data processing apparatus according to claim 1, wherein the score values are inner products between each of the plurality of spectra and each of the plurality of second base vectors.

9. The data processing apparatus according to claim 1, wherein the scores are principal component scores.

10. A data processing apparatus for processing data including a plurality of spectra, comprising:
a processor; and
a memory,
wherein the processor receives the data including the plurality of spectra and stores the data in the memory,
wherein the processor performs a first multivariate analysis on the data stored in the memory to obtain a plurality of second base vectors,
wherein the first multivariate analysis at least includes a principal component analysis,
wherein the processor classifies the plurality of spectra included in the data stored in the memory into a plurality of groups using the plurality of second base vectors;
wherein the processor generates extracted data by extracting a part of the plurality of spectra from each of the plurality of groups, wherein a size of the extracted data is smaller than that of the data stored in the memory,
wherein the processor performs a second multivariate analysis on the extracted data to obtain a plurality of first base vectors from the extracted data, and
wherein the second multivariate analysis includes at least both a principal component analysis and an independent component analysis.

11. A data processing apparatus for processing data including a plurality of spectra, comprising:
a processor; and
a memory,
wherein the processor receives first data including a plurality of first spectra in a first region including a sample and second data including a plurality of second spectra in a second region, the second region including more measurement points than the first region, and stores the first data and the second data in the memory,
wherein the processor performs a first multivariate analysis on the first data stored in the memory to obtain a plurality of second base vectors,
wherein the processor generates extracted data by extracting a part of the plurality of first spectra from the first data stored in the memory using the plurality of second base vectors,
wherein a size of the extracted data is smaller than that of the first data stored in the memory,
wherein the processor performs a second multivariate analysis on the extracted data to obtain a plurality of first base vectors from the extracted data,
wherein the second multivariate analysis includes at least both a principal component analysis and an independent component analysis; and
wherein the processor performs an obtaining process based on the second data stored in the memory and the plurality of first base vectors to obtain independent component scores of the second data.

12. The data processing apparatus according to claim 11,
wherein the processor classifies the plurality of first spectra included in the first data stored in the memory into a plurality of groups using the plurality of second base vectors; and
wherein the processor generates the extracted data by extracting the part of the plurality of first spectra from each of the plurality of groups.

13. The data processing apparatus according to claim 11,
wherein the processor classifies the plurality of first spectra included in the first data stored in the memory into a plurality of groups based on score values obtained from each of the plurality of first spectra and each of the plurality of second base vectors, and
wherein the processor generates the extracted data by extracting the part of the plurality of first spectra from each of the plurality of groups.

14. The data processing apparatus according to claim 11, wherein the first region and the second region include an entirety of a region in which the sample exists.

15. The data processing apparatus according to claim 11, wherein the second region is included in the first region.

16. The data processing apparatus according to claim 11, wherein the second region overlaps with the first region.

17. The data processing apparatus according to claim 11, wherein an image of the independent component scores is displayed based on the independent component scores and based on positional information corresponding to the independent component scores.

* * * * *